(12) United States Patent
McNeish et al.

(10) Patent No.: US 6,927,317 B2
(45) Date of Patent: Aug. 9, 2005

(54) MODULATING RAMP ACTIVITY

(75) Inventors: John D. McNeish, Mystic, CT (US);
Walter C. Soeller, Mystic, CT (US);
John F. Thompson, Warwick, RI (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/006,542

(22) Filed: Nov. 30, 2001

(65) Prior Publication Data

US 2002/0178459 A1 Nov. 28, 2002

Related U.S. Application Data

(60) Provisional application No. 60/250,965, filed on Nov. 30, 2000.

(51) Int. Cl.[7] .......................... A01K 67/027; C12N 5/00; C12N 5/02
(52) U.S. Cl. .......................................... 800/18; 435/325
(58) Field of Search ...................... 800/18, 14; 435/325

(56) References Cited

PUBLICATIONS http://www.bioscience.org/knockout/knochome.htm ; 1998.*
Pera, 2000, Journal of Cell Science, vol. 113, pp. 5–10.*
Chapman, 1989, PNAS, vol. 86, pp. 1292–1296.*
Leonard, 1995, Immunological Reviews, vol. 148, pp. 97–114.*
Griffiths, 1998, Microscopy Research and Technique, vol. 41, pp. 344–358.*
Capecchi, 1994, Scientific American, vol. 270, pp. 34–41.*
Hussman, 2000, Mol. Cell. Endocrin., vol. 162, pp. 35–43.*
Dinnyes, 2002, Cloning and Stem Cells, vol. 4, pp. 81–90.*
Campbell and Wilmut, 1997, Theriogenology, vol. 47, pp. 63–72.*
Kent–First, 2000, Nature Biotecnology, vol. 18, pp. 928–929.*
Denning, 2001, Nature Biotechnology, vol. 19, pp. 559–562.*
Partial European Search Report under Rule 46(1), European Patent Office, Application No. EP 01 30 9928, May 10, 2002.
Foord, Steven M., and Marshall, Fiona H., "RAMPs: accessory proteins for seven transmembrane domain receptors", Trends in Pharmacological Sciences, Elsevier Trends Journal, May 1, 1999, vol. 20, No. 5, pp. 184–187.

McLatchie, Linda M. et al., "RAMPS regulate the transport and ligand specificity of the calcitonin–receptor–like receptor", Nature, MacMillan Journals, Ltd., May 28, 1998, vol. 393, pp. 333–339.

Derst, C. et al., "Genomic structure and chromosome mapping of human and mouse RAMP genes", Cytogenics and Cell Genetics, vol. 90, No. 1–2, 2000, pp. 115–118.

Zumpe, Emma T. et al., "Multiple Ramp Domains Are Required for Generation of Amylin Receptor Phenotype from the Calcitonin Receptor Gene Product", Biochemical and Biophysical Research Communications, vol. 267, No. 1, Jan. 7, 2000, pp. 368–372.

Armour, Susan L. et al., "Pharmacological characterization of receptor–activity–modifying proteins (RAMPS) and the human calcitonin receptor", Journal of Pharmacological and Toxicological Methods, vol. 42, No. 4, Dec. 1999, pp. 217–224.

Frayon, Stéphane et al., "Dexamethasone Increases RAMP1 and CRLR mRNA Expressions in Human Vascular Smooth Muscle Cells", Biochemical and Biophysical Research Communications, vol. 270, No. 3, Apr. 21, 2000, pp. 1063–1067.

Kuwasako, Kenji et al., "Visualization of the Calcitonin Receptor–like Receptor and Its Receptor Activity–modifying Proteins during Internalization and Recycling", Journal of Biological Chemistry, vol. 275, No. 38, Sep. 22, 2000, pp. 29602–29609.

Tilakaratne, Nanda et al., "Amylin Receptor Phenotypes Derived from Human Calcitonin Receptor/RAMP Coexpression Exhibit Pharmacological Differences Dependent on Receptor Isoform and Host Cell Environment", Journal of Pharmacology and Experimental Therapeutics, vol. 294, No. 1, Jul. 2000, pp. 61–72.

* cited by examiner

*Primary Examiner*—Joseph Woitad
*Assistant Examiner*—Valarie Bertoglio
(74) *Attorney, Agent, or Firm*—Peter C. Richardson; Gregg C. Benson; Deborah A. Martin

(57) ABSTRACT

The invention provides genetically-modified non-human mammals and genetically-modified animal cells containing a disrupted RAMP1, RAMP2, or RAMP3 gene. Also provided by the invention are methods of screening for agents that modulate the activity or expression of a RAMP and methods of treating mammals to modulate liver function and/or muscle metabolism.

4 Claims, 6 Drawing Sheets

SEQ ID NO: 1
tcggcaggcctaggctcaacccagccancttgtgctnaggcctg
ctgccttttcaaagcncagtggtagctagttttgattatccaacc
tgacncaacantaaaattacttaaaaaggggntttntttttccatt
gggttggcctgtgggcatgtctgtgggaggctgtcgtaactgcac
tgtgggcagcaccattccctaggcagagagggtcctcaactgtgt
cagaatggagaaactgagtagagcacaagcaaatgaacacatatg
cattcactgttccctgctcttgtctgtggatgccatgtgaccacc
tgtgttacgttccttcctcccggagttgcttttatcacaacaaaa
tgaaactcagacaggtgttatctcctgatcacacagacacatt
tctgggaccctgggatgggctggaatggaggcggggagcaatgga
agaggccaccaaaggcaatgagagagagccagtaggtaacagccc
ttgtatgttttttgttttttgttttgttttgtttttttaca
gCTCACCATCTCTTCATGGTCACTGCCTGCCGGGACCCTGACTAT
GGGACTCTCATCCAGGAGCTGTGCCTCAGCCGCTTCAAGGAGAAC
ATGGAGACTATTGGGAAGACGCTATGGTGTGACTGGGGAAAGACC
ATACAgtgagtcctatcaggagagaaggaggctgggagacatgtc
ctctcctttacattggggcatcaggccactgggtctggggaaagc
cagagtctaaagggacaggatggagcggaaagggagcctcagtca
ttggcagatgtttatgacatgtgggtgggaggagctgtgtcttcg
atggctgtccaggtagccatgggtgccaggggagcaggagatgaa
gggttcagattagatatccatatagcaaccaagtgtaggcacctg
gggatgggtgagnccttatcaatggcttgaaccttgngtgactgn
ctttggacanaagccaggccttcagggatctccctgttggttcct
tccatcctgtggcaagccanactcctttc

FIG. 1

SEQ ID NO: 4
CTATCCCGCTGTTGCTGCAAGCCGGCTGCATCTTAGTTGGCCATGAAGACCCCAGCACAG
CGGCTGCACCTTCTTCCACTGTTGTTGCTGCTTTGTG.......AGAGGGATAGTATGTTGAAATCC
CAGGTGACAAGCAGCGTCAGGTCTCAGAGATTCTATGAACTTTCTCATTGCTGCAAACATGAATCCCAGTGGG
CCCCAGCCTCAGACCTCCAAGAATCCAGGCAGGTTATGACAGGCTGGGAGGTCTGTTCCAGCTCACATCCT
TTCTCAGGACTTCTGCAGGTACCCTGAGCTGGATTGAGTTGGGACTCCTGGATATTCCCAGGACCTCT
GCCAGCTCCTGATGACTCTGGCCCAGGGCCTCCCTGTGCCTTTCTCCTTGTGTCATTGCTGTGGTCCAGT
GGCCAGGGTTGAGGGTGAACTCTGGCTGGTGATGCCTATCAGTGGGAGGGCTATGCTTACATCAGCAAGG
GGTGGGGCTGTGCTAGTCAGAGTTTCCTGGACATCCCCTTCCACTGTGTCCCCTCC[AG]GTGAGTGTG
CCCAGGTATGCGGCTGACATGATGCAGAAGGTGCTGTCTGGAGAGGCTGCCTGCTGTGGGAGTTCAT
CCTTCGCTGACATGATGCAGAAGGTGGCTGTCTGGAAGTGGTGCACCTGCCCTGTACCTTGCCCCTC
CGT[GTGAGT]GCCCAGCTGGTCACGATCCTGGGCACACTCACCCTCAGGCCTCACTGTGCCCATAATCCCACC
CCATACTTCTGCTCTGAGCTGCAGCTGCAGTTCAATGGGGTCAGTTGGGCTTANCCACATAGAGCTGTGAGAACAGTGTG
GCAGTGTTTCTGGGCAGTTGGGCAGTTCTTGAAACACGGGAGGAGGGTGTCACAGTACATGCATC
TTAACACATGGAGACCAACATCATGGGGCTTTGA.......GTATTATGAAAGCTTCACTAACTGCACCGAGA
TGGAGACCAACATCATGGGGCTACTGGCCCAACCCGCTGCCCCAGAGCTTCATCACTG
GAATCCACAGGCAGTTCTTTCCAACTGCACGGTGGACAGGACCCACTGGGAAGACCCCC
CGGATGAAGTAGTACTCATCCCACACTGATCGCGGTTCCTGTCGTGCTGACTGTGGCTATGGCTG
GCCTGGTGGTGTGTGGCCCAGGCAAGCACACTGATCGCTGTCGTGAGGATCGCTGGATGAGGGCC
ATGCCTGGCAGGCTGGGAGAATGTGCTGAGAGCTGAGACTCGGCTTCGTCTGTCTGTTTTGCT
TTGGCCACACCCTACCCGCCATGCCAAAGTCCTCCTGACCAGGCTGGTGGCCCTTGCTGTGGCTGC
CGCCTGCTCGGGGTTCAAATTGTCCATACTTTGCTCTTTCTT

FIG. 4

SEQUENCE LISTING

<160> NUMBER OF SEQ ID NOS: 8

<210> SEQ ID NO 1
<211> LENGTH: 1064
<212> TYPE: DNA
<213> ORGANISM: Mus Musculus
<220> FEATURE:
<221> NAME/KEY: misc_feature
<222> LOCATION: (29)..(10555)
<223> OTHER INFORMATION: At position 29,38,61,95,101,122,126,958,982, 990,1000 & 1055 'n' equals c,t,a or g

<400> SEQUENCE: 1

```
tcggcaggcc taggctcaac cccagccanc ttgtgctnag gcctgctgcc ttttcaaagc    60
ncagtggtag ctagttttga ttatccaacc tgacncaaca ntaaaattac ttaaaaaggg   120
gntttntttt ccattgggtt ggcctgtggg catgtctgtg ggaggctgtc gtaactgcac   180
tgtgggcagc accattccct aggcagagag ggtcctcaac tgtgtcagaa tggagaaact   240
gagtagagca caagcaaatg aacacatatg cattcactgt tccctgctct tgtctgtgga   300
tgccatgtga ccacctgtgt tacgttcctt cctcccggga ttgcttttat cacaacaaaa   360
tgaaactcag acaggtgtta tctcctgatc acacagacac acatttctgg gaccctggga   420
tgggctggaa tggaggcggg gagcaatgga agaggccacc aaaggcaatg agagagagcc   480
agtaggtaac agcccttgta tgttttttttg ttttttttgtt tttgttttg tttttttaca   540
gctcaccatc tcttcatggt cactgcctgc cgggaccctg actatgggac tctcatccag   600
gagctgtgcc tcagccgctt caaggagaac atggagacta ttgggaagac gctatggtgt   660
gactggggaa agaccataca gtgagtccta tcaggagaga aggaggctgg gagacatgtc   720
ctctccttta cattggggca tcaggccact gggtctgggg aaagccagag tctaaaggga   780
caggatggag cggaaaggga gcctcagtca ttggcagatg tttatgacat gtgggtggga   840
ggagctgtgt cttcgatggc tgtccaggta gccatgggtg ccaggggagc aggagatgaa   900
gggttcagat tagatatcca tatagcaacc aagtgtaggc acctgggat gggtgagncc    960
ttatcaatgg cttgaacctt gngtgactgn ctttggacan aagccaggcc ttcagggatc  1020
tccctgttgg ttccttccat cctgtggcaa gccanactcc tttc                   1064
```

<210> SEQ ID NO 2
<211> LENGTH: 10
<212> TYPE: DNA
<213> ORGANISM: Mus musculus

<400> SEQUENCE: 2

```
ctgcctgccg                                                          10
```

<210> SEQ ID NO 3
<211> LENGTH: 10
<212> TYPE: DNA
<213> ORGANISM: Mus musculus

<400> SEQUENCE: 3

```
gactatggga                                                          10
```

<210> SEQ ID NO 4
<211> LENGTH: 1450
<212> TYPE: DNA
<213> ORGANISM: Mus Musculus
<220> FEATURE:
<221> NAME/KEY: misc_feature
<222> LOCATION: (859)..(859)
<223> OTHER INFORMATION: At position number 859 'n' equals c, t, a or g

<400> SEQUENCE: 4

```
ctatcccgct gttgctgcaa gccggctgca tcttagttgg ccatgaagac cccagcacag    60
cggctgcacc ttcttccact gttgttgctg ctttgtgaga ggggatagta tgttgaaatc   120
ccaggtgaca agcagcgtca ggtctcagga ttctatgaac tttctcattg ctgcaaacat   180
gaatcccagt gggccccagc ctcagacctc caagaatcca ggcaggttat gacagggctg   240
```

```
ggaggtctgt tccagctcac atcctttctc aggacttctg caggtaccct gagctactgg      300
attgagttgg ggactcctgg atattcccag gacctctgcc agctcctgat gactctggcc      360
cagggcctcc ctgtggcttt ctctccttgt gtcattgctg tggtccagtg gccaggttg       420 agggtgaact ctggctggtg atggcctatc agtgggaggg gctatgctta catcagcaag      480
gggtggggct gtgctagtca gagtttcctg gacatccctc ttctcactgt tgtccctcct      540
aggtgagtgt gcccaggtat gcggctgcaa cgagacaggg atgctggaga ggctgcctcg      600
ctgtgggaaa gccttcgctg acatgatgca aaggtggct gtctggaagt ggtgcacctg       660
tcggagttca tcgtgtgagt gcccagctgg tcacgggacc cagccattgt gccgcatgcc      720
tagccctgta ccttgcccc tcccatactt ctgctcacga tcctgggcac actcacccctc      780 aggcctccca taatccccac ccatctctgc ccacacactg ctctgagctg cagggtatc      840 tggggtctgt ttggcttanc cacatagagc tgtgagaaca gttgtgggca gtgtttctgg      900
gcagttcaat ggaaaggtct tggaaacacg ggaggagggg tgtcacagta catgcatctt      960
aacacacatg gagaggaggg ggctttgagt attatgaaag cttcactaac tgcaccgaga     1020
tggagaccaa catcatgggc tgctactggc ccaacccgct ggcccagagc ttcatcactg     1080
gaatccacag gcagttcttt tccaactgca cggtggacag gacccactgg gaagacccc      1140 cggatgaagt actcatccca ctgatcgcgg ttcctgtcgt gctgactgtg ctatggctg      1200 gcctggtggt gtggcgcagc aagcacactg atcggctgct gtgaggatct gctggatgga     1260
gggccatgcc tggcaggctg ggagaatgtt gctcagagct ctgagagctg cagactcgg      1320 cttctgtctg gtttgctttg ccacaccct acccggccat gccaaagtcc tcctgaccag     1380
gctggtgtgg cccttgctgt ctagcctgcc gcctgctggg gttcaaattg tccatacttt     1440
gctctttctt                                                            1450
```

`<210>` SEQ ID NO 5
`<211>` LENGTH: 10
`<212>` TYPE: DNA
`<213>` ORGANISM: Mus musculus

`<400>` SEQUENCE: 5

```
ccaggtatgc                                                              10
```

`<210>` SEQ ID NO 6
`<211>` LENGTH: 10
`<212>` TYPE: DNA
`<213>` ORGANISM: Mus musculus

`<400>` SEQUENCE: 6

```
caactgcacg                                                              10
```

`<210>` SEQ ID NO 7
`<211>` LENGTH: 10
`<212>` TYPE: DNA
`<213>` ORGANISM: Mus Musculus

`<400>` SEQUENCE: 7

```
gcagaactgc                                                              10
```

`<210>` SEQ ID NO 8
`<211>` LENGTH: 10
`<212>` TYPE: DNA
`<213>` ORGANISM: Mus Musculous

```
<400> SEQUENCE: 8
catccttgag                                                                      10
```

MODULATING RAMP ACTIVITY

This application claims priority, under 35 U.S.C. §119 (e), from U.S. provisional application 60/250,965, which was filed Nov. 30, 2000.

FIELD OF THE INVENTION

The present invention relates to genetically-modified non-human mammals and genetically-modified animal cells containing a disrupted RAMP gene. The invention also features methods of screening for agents that modulate RAMP activity and methods of modulating RAMP function in cells that express a RAMP1, RAMP2, or RAMP3 gene.

BACKGROUND OF THE INVENTION

The receptor-activity-modifying protein (RAMP) family is currently understood to comprise three members (RAMP1, RAMP2, and RAMP3); they are single transmembrane domain proteins that associate with certain G-protein coupled receptors and influence receptor function. For example, RAMPs are required to transport the calcitonin receptor-like receptor (CRLR) to the plasma membrane. The phenotype of the CRLR varies depending upon which RAMP is involved in its transport. For example, RAMP1 transported CRLR exhibits a calcitonin gene-related peptide (CGRP) receptor phenotype, whereas RAMP2 or RAMP3 transported CRLR exhibits an adrenomedullin receptor phenotype (McLatchie et al., Nature 393: 333–339, 1998; Christopoulos et al., Mol. Pharmacol. 56: 235–42,1999). In addition, RAMP1 and RAMP3, but not RAMP-2, also associate with the calcitonin (CT) family of receptors, increasing receptor specificity for amylin (islet amyloid polypeptide) and decreasing specificity for calcitonin (Muff et al., Endocrinology 140: 2924–27, 1999).

Further study is required to understand the complex role of RAMPs in the function of some G-protein coupled receptors and the therapeutic implications associated with these functions. Accordingly, the present invention provides biological tools to study RAMP1, RAMP2, and RAMP3 function and methods to identify agents that regulate these RAMPs for use in treating diseases and conditions that are linked to these functions.

SUMMARY OF THE INVENTION

The present invention features genetically-modified animal cells and genetically-modified non-human mammals containing a disrupted RAMP1, RAMP2, or RAMP3 gene, as well as assays for identifying agents that modulate the activity of one of these RAMP genes, and methods of treating or preventing diseases or conditions in mammals by modulating one or more of these RAMP proteins. In the first aspect, the invention features a genetically-modified, non-human mammal, wherein the modification results in a disrupted RAMP1 or RAMP3 gene. The mammal is either heterozygous or homozygous for the modification. Preferably, the mammal is a rodent, more preferably, a mouse. Preferably, the mammal expresses an exogenous reporter gene under the control of the regulatory sequences of the RAMP1 or RAMP3 gene. The invention also features a genetically-modified, non-human mammal that is heterozygous for a genetic modification which results in a disrupted RAMP2 gene and results in expression of an exogenous reporter gene under the control of the regulatory sequences of the RAMP2 gene. Preferably, the mammal is a mouse. In a second and related aspect, the invention provides a genetically-modified animal cell, wherein the modification comprises a disrupted RAMP1, RAMP2, or RAMP3 gene. The animal cell is heterozygous or homozygous for the modification. Preferably, the cell is an embryonic stem (ES) cell, the cell is human, or the cell is murine. The invention also features a membrane preparation derived from the modified animal cell.

In another aspect, the invention features a method of treating a disorder associated with liver function and/or muscle metabolism in a mammal. The method involves administering an agent that modulates RAMP1 activity. Preferably, the agent increases RAMP1 activity and is administered to treat or prevent congestive heart failure, mitral stenosis, acute myocardial infarction, hypertension, chronic or acute hepatitis, hepatomegaly, hepatic steatosis, biliary atresia, gallstones, and/or chemical or drug-induced hepatotoxicity.

Other aspects of the invention provide: (a) a method of modulating RAMP1 activity in a mammal in cells of the striatum, the cerebral cortex, the central liver vein smooth muscle layer, the female or male reproductive tract, or the skin, involving administering to the cells in the mammal an agent that modulates RAMP1 activity; (b) a method of modulating RAMP2 activity in a mammal in spermatogenic cells, involving administering to the cells an agent that modulates RAMP2 activity; and (c) a method of modulating RAMP3 activity in a mammal in cells of the caudate putamen, the laterodorsal thalamic region of the cerebrum, or in the male reproductive tract, involving administering to the cells in the mammal an agent that modulates RAMP3 activity.

In related aspects, the invention provides: (a) a method of identifying an agent that modulates RAMP1 activity, involving contacting the agent with a cell from the striatum, the cerebral cortex, the central liver vein smooth muscle layer, the gallbladder, the female or male reproductive tract, or the skin, and measuring RAMP1 activity; wherein a difference between the activity in the absence of the agent and in the presence of the agent is indicative that the agent can modulate RAMP1 activity; (b) a method of identifying an agent that modulates RAMP2 activity, involving contacting the agent with a spermatogenic cell and measuring RAMP2 activity, wherein a difference between the activity in the absence of the agent and in the presence of the agent is indicative that the agent can modulate RAMP2 activity; and (c) a method of identifying an agent that modulates RAMP3 activity, involving contacting the agent with a cell from the caudate putamen, the laterodorsal thalamic region of the cerebrum, or the male reproductive tract, and measuring RAMP3 activity, wherein a difference between the activity in the absence of the agent and in the presence of the agent is indicative that the agent can modulate RAMP3 activity.

Other related aspects of the invention feature: (a) a method of identifying an agent that modulates RAMP1 gene expression, involving contacting an agent with a cell from the striatum, the cerebral cortex, the central liver vein smooth muscle layer, the female or male reproductive tract, or the skin, that expresses a coding sequence under the control of a RAMP1 gene regulatory sequence, and measuring expression of the coding sequence, wherein a difference between the expression in the absence of the agent and in the presence of the agent is indicative that the agent can modulate RAMP1 gene expression; (b) a method of identifying an agent that modulates RAMP2 gene expression, involving contacting an agent with a spermatogenic cell that expresses a coding sequence under the control of a RAMP2 gene regulatory sequence, and measuring expression of the coding sequence, wherein a difference between the expression in the absence of the agent and in the presence of the agent is indicative that the agent can modulate RAMP2 gene expression; and (c) a method of identifying an agent that modulates RAMP3 gene expression, involving contacting an agent with a cell from the caudate putamen, the laterodorsal thalamic region of the cerebrum, or the male reproductive tract, that expresses a coding sequence under the control of a RAMP3 gene regulatory sequence, and measuring expression of the coding sequence, wherein a difference between the expression in the absence of the agent and in the presence of the agent is indicative that the agent can modulate RAMP3 gene expression. Preferably, the coding sequence encodes a reporter polypeptide.

And the invention also provides: a method of confirming whether an agent identified as modulating RAMP1 activity mediates its effect through RAMP1, involving contacting the agent with a genetically-modified non-human mammal, or animal cell, or membrane preparation from the animal cell, that is homozygous for a genetic disruption of the RAMP1 gene, wherein the absence of an effect on RAMP1 activity in the genetically-modified mammal, or animal cell, or membrane preparation, that is present in the wild type non-human mammal, animal cell, or membrane preparation confirms that the agent mediates its effect through RAMP1; and a method of confirming whether an agent identified as modulating RAMP3 activity mediates its effect through RAMP3, involving contacting the agent with a genetically-modified non-human mammal, or animal cell, or membrane preparation from the animal cell, that is homozygous for a genetic disruption of the RAMP3 gene, wherein the absence of an effect on RAMP3 activity in the genetically-modified mammal, or animal cell, or membrane preparation, that is present in the wild type non-human mammal, animal cell, or membrane preparation confirms that the agent mediates its effect through RAMP3.

In addition, another aspect of the invention provides: a method of identifying the in vivo roles of RAMP1 and RAMP3 in calcitonin receptor-mediated amylin signalling, involving comparing the amylin signalling response in a genetically-modified non-human mammal that is homozygous for a disruption of the RAMP1 gene, and/or in a genetically-modified non-human mammal that is homozygous for a disruption of the RAMP3 gene, to a wild type non-human mammal; and a method of identifying the in vivo roles of RAMP2 and RAMP3 in calcitonin receptor like receptor-mediated adrenomedullin signalling, involving comparing the adrenomedullin signalling response in a genetically-modified non-human mammal that is homozygous for a disruption of the RAMP3 gene to a wild type non-human mammal.

Those skilled in the art will fully understand the terms used herein in the description and the appendant claims to describe the present invention. Nonetheless, unless otherwise provided herein, the following terms are as described immediately below.

A non-human mammal or an animal cell that is "genetically-modified" is heterozygous or homozygous for a modification that is introduced into the non-human mammal or animal cell, or into a progenitor non-human mammal or animal cell, by genetic engineering. The standard methods of genetic engineering that are available for introducing the modification include homologous recombination, viral vector gene trapping, irradiation, chemical mutagenesis, and the transgenic expression of a nucleotide sequence encoding antisense RNA alone or in combination with catalytic ribozymes. Preferred methods for genetic modification are those which modify an endogenous gene by inserting a "foreign nucleic acid sequence" into the gene locus, e.g., homologous recombination and viral vector gene trapping. A "foreign nucleic acid sequence" is an exogenous sequence that is non-naturally occurring in the gene to be modified. This insertion of foreign DNA can occur within any region of the gene, e.g., in an enhancer, promoter, regulator region, noncoding region, coding region, intron, or exon. The most preferred method of genetic engineering is homologous recombination, in which the foreign nucleic acid sequence is inserted in a targeted manner either alone or in combination with specific nucleotide changes to, or a deletion of, a portion of the endogenous gene sequence.

By a RAMP1, RAMP2, or RAMP3 gene that is "disrupted" is meant a RAMP gene that is genetically-modified such that the cellular activity of the respective RAMP polypeptide encoded by the disrupted gene is decreased in cells that normally express a wild type version of the RAMP gene. When the genetic modification effectively eliminates all wild type copies of the RAMP gene in a cell (e.g., the genetically-modified, non-human mammal or animal cell is homozygous for the RAMP gene disruption or the only wild type copy of RAMP gene originally present is now disrupted), then the genetic modification results in a reduction in the polypeptide activity of the RAMP as compared to an appropriately matched cell that expresses the wild type RAMP gene. This reduction in RAMP polypeptide activity results from either reduced RAMP gene expression (i.e., reduced RAMP mRNA levels produce reduced levels of the RAMP polypeptide) and/or because the disrupted RAMP gene encodes a mutated polypeptide with reduced function as compared to a wild type RAMP polypeptide. Preferably, the activity of the RAMP1, RAMP2, or RAMP3 polypeptide in the genetically-modified, non-human mammal or animal cell is reduced to 50% or less of wild type levels, more preferably, to 25% or less, and, even more preferably, to 10% or less of wild type levels. Most preferably, the polypeptide activity is nondetectable in a genetically-modified, non-human mammal or animal cell that is homozygous for the gene disruption.

By a "genetically-modified, non-human mammal" containing a disrupted RAMP1, RAMP2, or RAMP3 gene is meant a non-human mammal that is produced, for example, by creating a blastocyst carrying the desired genetic modification and then implanting the blastocyst in a foster mother for in utero development. The genetically-modified blastocyst can be made, in the case of mice, by implanting a genetically-modified embryonic stem (ES) cell into a mouse blastocyst. Alternatively, various species of genetically-modified embryos can be obtained by nuclear transfer. In the case of nuclear transfer, the donor cell is a somatic cell or a pluripotent stem cell, and it is engineered to contain the desired genetic modification that disrupts the RAMP gene. The nucleus of this cell is then transferred into a fertilized or parthenogenetic oocyte that is enucleated, the embryo is reconstituted, and developed into a blastocyst. A genetically-modified blastocyst produced by either of the above methods is then implanted into a foster mother according to standard methods known to those of skill in the art. A "genetically-modified, non-human mammal" includes all progeny of the mammals created by the methods described above, provided that the progeny inherit at least one copy of the genetic modification that disrupts the RAMP gene. It is preferred that all somatic cells and germline cells of the genetically-modified mammal contain the modification. Preferred non-human mammals that are genetically-modified to contain a disrupted RAMP gene include rodents, such as mice and rats, cats, dogs, rabbits, guinea pigs, hamsters, pigs, sheep, and ferrets.

By a "genetically-modified animal cell" containing a disrupted RAMP1, RAMP2, or RAMP3 gene is meant an animal cell, including a human cell, created by genetic engineering to contain a disrupted gene, as well as daughter cells that inherit the gene. These cells may be genetically-modified in culture according to any standard method known in the art. As an alternative to genetically modifying the cells in culture, non-human mammalian cells may also be isolated from a genetically-modified, non-human mammal that contains the desired RAMP gene disruption. The animal cells of the invention may be obtained from primary cell or tissue preparations as well as culture-adapted and/or transformed cell lines. These cells and cell lines are derived, for example, from endothelial cells, epithelial cells, islets, neurons and other neural tissue-derived cells, mesothelial cells, osteocytes, lymphocytes, chondrocytes, hematopoietic cells, immune cells, cells of the major glands or organs (e.g., liver, lung, heart, stomach, pancreas, testis, ovary, kidney, and skin), muscle cells (including cells from skeletal muscle, smooth muscle, and cardiac muscle), exocrine or endocrine cells, fibroblasts, and embryonic and other totipotent or pluripotent stem cells (e.g., ES cells, ES-like cells, and embryonic germline (EG) cells, and other stem cells, such as progenitor cells and tissue-derived stem cells). The preferred genetically-modified cells are ES cells, more preferably, mouse or rat ES cells, and, most preferably, human ES cells.

By an "ES cell" or an "ES-like cell" is meant a pluripotent stem cell derived from an embryo, from a primordial germ cell, or from a teratocarcinoma, that is capable of indefinite self renewal as well as differentiation into cell types that are representative of all three embryonic germ layers.

By "reduced" is meant a statistically significant decrease (i.e., p<0.1, preferably, p<0.05).

By "modulates" is meant a statistically significant increase or decrease (including a complete elimination).

By "measuring expression" is meant measuring mRNA levels or levels of the polypeptide encoded by the mRNA.

By "RAMP1 polypeptide activity" "RAMP1 activity" or "RAMP1 polypeptide-like activity" is meant an increase in CGRP binding to the CRLR, an increase in cAMP, and/or an increase in inward current that is mediated by the polypeptide encoded by the RAMP1 gene. Such activity can be modulated in a cell at the level of expression (e.g., by changing the level of polypeptide that is present within a cell) or by modifying the particular functional characteristics of each RAMP1 polypeptide molecule (e.g., binding affinity or cellular signalling activity).

By "RAMP2 polypeptide activity" "RAMP2 activity" or "RAMP2 polypeptide-like activity" is meant an increase in adrenomdullin binding to the calcitonin receptor-like receptor (CRLR), an increase in cAMP and/or an increase in the inward current that is mediated by the polypeptide encoded by the RAMP2 gene. Such activity can be modulated in a cell at the level of expression (e.g., by changing the level of polypeptide that is present within a cell) or by modifying the particular functional characteristics of each RAMP2 polypeptide molecule (e.g., binding affinity or cellular signalling activity).

By "RAMP3 polypeptide activity" "RAMP3 activity" or "RAMP3 polypeptide-like activity" is meant an increase in adrenomedullin binding to the CRLR, an increase in cAMP, and/or an increase in inward current that is mediated by the polypeptide encoded by the RAMP3 gene. Such activity can be modulated in a cell at the level of expression (e.g., by changing the level of polypeptide that is present within a cell) or by modifying the particular functional characteristics of each RAMP3 polypeptide molecule (e.g., binding affinity or cellular signalling activity).

By "regulatory sequences" is meant promoter sequences and/or other sequences (e.g., enhancers) that mediate the endogenous expression of the gene.

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art, and that can be ascertained without undue experimentation. Additional guidance with respect to making and using nucleic acids and polypeptides is found in standard textbooks of molecular biology, protein science, and immunology (see, e.g., Davis et al., Basic Methods in Molecular Biology, Elsevir Sciences Publishing, Inc., New York, N.Y.,1986; Hames et al., Nucleic Acid Hybridization, IL Press, 1985; Molecular Cloning, Sambrook et al., Current Protocols in Molecular Biology, Eds. Ausubel et al., John Wiley and Sons; Current Protocols in Human Genetics, Eds. Dracopoli et al., John Wiley and Sons; Current Protocols in Protein Science, Eds. John E. Coligan et al., John Wiley and Sons; and Current Protocols in Immunology, Eds. John E. Coligan et al., John Wiley and Sons). All references mentioned herein are incorporated by reference.

DESCRIPTION OF THE DRAWINGS

FIG. 1 shows a partial murine RAMP1 genomic sequence (SEQ ID NO: 1). Exon coding sequence is shown in uppercase letters and putative intron sequence is shown in lower case letters. Splice site consensus sequences are are enclosed in boxes, and exon sequence targeted for deletion and replacement with LacZ-Neo is double underlined.

FIG. 4 shows the partial murine genomic sequence for RAMP3 (SEQ ID NO: 4). Letters in large font represent cDNA exon coding sequence; letters in smaller font represent putative intron sequence. Splice site consensus sequences are enclosed in boxes. Exon and intron sequence targeted for deletion and replacement by LacZ-Neo are double underlined. Gaps in the intron sequences are designated by ". . ."

DETAILED DESCRIPTION

Figure 2:
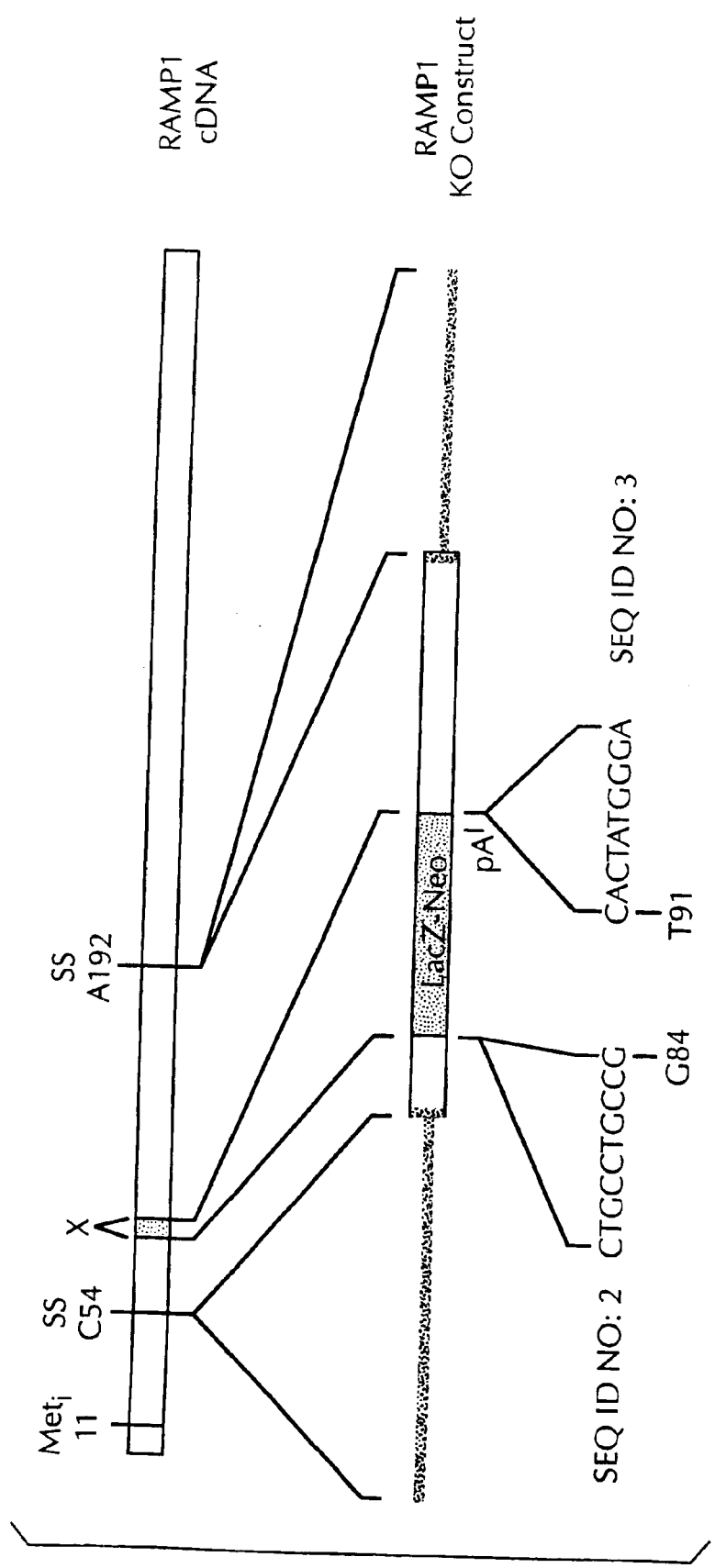
FIG. 2 is a schematic representation of the targeting construct used for homologous recombination with, and the disruption of, the RAMP1 gene. The region "X" represents the endogenous coding sequence targeted for deletion and replacement with LacZ-Neo. SS refers to putative splice sites. Numbers following nucleotide letters refer to the nucleotide position in the original mouse cDNA (top). pA in the targeting (KO) construct (bottom) refers to a polyadenylation signal used to truncate transcripts. SEQ ID NOs: 2 and 3 designate the sequences used as homology arms in the targeting construct.

The present invention provides genetically-modified, non-human mammals that are either heterozygous or homozygous for a genetic modification that disrupts either the RAMP1 or RAMP3 gene. In addition, the invention features genetically-modified non-human mammals that are heterozygous for a genetic modification that disrupts the RAMP2 gene and causes a reporter gene coding sequence to be expressed instead under the control of the RAMP2 promoter/regulatory sequences. The present invention also provides genetically-modified animal cells, including human cells, that are heterozygous or homozygous for a modification that disrupts the RAMP1, RAMP2, or RAMP3 gene. Preferably, the heterozygous cells are genetically-modified such that a reporter gene coding sequence is expressed instead of the RAMP coding sequence under the control of the RAMP promoter/regulatory sequence(s). The animal cells may be derived by genetically engineering cells in culture, or, in the case of non-human mammalian cells, the cells may be isolated from the above-described genetically-modified, non-human mammals.

The invention also provides methods for treating or preventing diseases or conditions, and/or symptoms of such diseases or conditions, associated with abnormal RAMP1, RAMP2, or RAMP3 activity by administering an agent that modulates the respective RAMP1, RAMP2, or RAMP3 activity. Specifically, based upon phenotypic studies of genetically-modified mice homozygous for a RAMP1 disruption (RAMP1−/−), we have discovered that RAMP1 plays a role in liver function and muscle metabolism. Accordingly, the present invention provides methods for treating or preventing diseases or conditions, and/or symptoms, of the cardiac, skeletal, or smooth muscle, such as congestive heart failure, mitral stenosis, acute myocardial infarction, and vascular and cardiovascular disorders such as hypertension, by administering an agent that modulates RAMP1 activity. The present invention also provides methods for treating or preventing hepatocellular disorders or conditions, and/or their symptoms, such as chronic and acute hepatitis, hepatomegaly, hepatic steatosis, biliary atresia, gallstones, and chemical or drug-induced hepatotoxicity, by administering an agent that modulates RAMP1 activity.

The genetically-modified, non-human mammals and the genetically-modified animal cells of the invention have at least one RAMP1, RAMP2, or RAMP3 gene locus that is disrupted by one of the several techniques for genetic modification known in the art, including chemical mutagenesis (Rinchik, Trends in Genetics 7: 15–21, 1991, Russell, Environmental & Molecular Mutagenesis 23 (Suppl. 24) 23–29, 1994), irradiation (Russell, supra), transgenic expression of RAMP1 or RAMP3 gene antisense RNA, either alone or in combination with a catalytic RNA ribozyme sequence (Luyckx et al., Proc. Natl. Acad. Sci. 96: 12174–79, 1999; Sokol et al., Transgenic Research 5: 363–71, 1996; Efrat et al., Proc. Natl. Acad. Sci. USA 91: 2051–55,1994; Larsson et al., Nucleic Acids Research 22: 2242–48, 1994) and, as further discussed below, by the insertion of a foreign nucleic acid sequence into the RAMP1 or RAMP3 gene locus. Preferably, the foreign sequence is inserted by homologous recombination or by the insertion of a viral vector. Most preferably, the method of gene disruption is homologous recombination and includes a deletion of a portion of the endogenous RAMP1 or RAMP3 gene sequence.

The integration of the foreign sequence disrupts the RAMP1 or RAMP3 gene through one or more of the following mechanisms: by interfering with the RAMP gene transcription or translation process (e.g., by interfering with promoter recognition, or by introducing a transcription termination site or a translational stop codon into the RAMP gene); or by distorting the RAMP gene coding sequence such that it no longer encodes a RAMP1 or RAMP3 polypeptide with normal function (e.g., by inserting a foreign coding sequence into the RAMP gene coding sequence, by introducing a frameshift mutation, or, in the case of a double crossover event, by deleting a portion of the RAMP gene coding sequence that is required for expression of a functional RAMP1 or RAMP3 protein).

To insert a foreign sequence into a RAMP gene locus of a cell's genome, the foreign DNA sequence is introduced into the cell by any suitable method, including those well known in the art such as electroporation, calcium-phosphate precipitation, retroviral infection, microinjection, biolistics, liposome transfection, DEAE-dextran transfection, or transferrinfection (see, e.g., Neumann et al., EMBO J. 1: 841–845,1982; Potter et al., Proc. Natl. Acad. Sci USA 81: 7161–65,1984; Chu et al., Nucleic Acids Res. 15: 1311–26, 1987; Thomas and Capecchi, Cell 51: 503–12, 1987; Baum et al., Biotechniques 17: 1058–62, 1994; Biewenga et al., J. Neuroscience Methods 71: 67–75, 1997; Zhang et al., Biotechniques 15: 868–72, 1993; Ray and Gage, Biotechniques 13: 598–603, 1992; Lo, Mol. Cell. Biol. 3: 1803–14, 1983; Nickoloff et al., Mol. Biotech. 10: 93–101,1998; Linney et al., Dev. Biol. (Orlando) 213: 207–16, 1999; Zimmer and Gruss, Nature 338: 150–153, 1989; and Robertson et al., Nature 323: 445–48, 1986). The preferred method for introducing foreign DNA into a cell is electroporation.

Exemplary Methods of Inserting DNA into a RAMP Gene

1. Homologous Recombination

The method of homologous recombination targets the RAMP1 or RAMP3 gene for disruption by introducing a RAMP gene targeting vector into a cell containing a RAMP gene. The ability of the vector to target the RAMP gene for disruption stems from using a nucleotide sequence in the vector that is homologous to the gene. This homology region facilitates hybridization between the vector and the endogenous sequence of the RAMP1 or RAMP3 gene. Upon hybridization, the probability of a crossover event between the targeting vector and genomic sequences greatly increases. This crossover event results in the integration of the vector sequence into the gene locus and the functional disruption of the RAMP1 or RAMP3 gene.

As those skilled in the art will appreciate, general principles regarding the construction of vectors used for targeting are reviewed in Bradley et al. (Biotechnol. 10: 534, 1992). Two different types of vector can be used to insert DNA by homologous recombination: an insertion vector or a replacement vector. An insertion vector is circular DNA which contains a region of gene homology with a double stranded break. Following hybridization between the homology region and the endogenous RAMP gene, a single crossover event at the double stranded break results in the insertion of the entire vector sequence into the endogenous gene at the site of crossover.

The more preferred vector to use for homologous recombination is a replacement vector, which is colinear rather than circular. Replacement vector integration into the RAMP1 or RAMP3 gene requires a double cross-over event, i.e. crossing over at two sites of hybridization between the targeting vector and the RAMP gene. This double crossover event results in the integration of vector sequence that is sandwiched between the two sites of crossover into the RAMP1 or RAMP3 gene and the deletion of the corresponding endogenous RAMP gene sequence that originally spanned between the two sites of crossover (see, e.g., Thomas and Capecchi et al., Cell 51: 503–12, 1987; Mansour et al., Nature 336: 348–52, 1988; Mansour et al., Proc. Natl. Acad. Sci. USA 87: 7688–7692, 1990; and Mansour, GATA 7: 219–227, 1990).

A region of homology in a targeting vector is generally at least 100 nucleotides in length. Most preferably, the homology region is at least 1–5 kilobases (kb) in length. There is no demonstrated minimum length or minimum degree of relatedness required for a homology region. However, as those skilled in the art will appreciate, targeting efficiency for homologous recombination generally corresponds with the length and the degree of relatedness between the targeting vector and the targeted gene locus. In the case where a replacement vector is used, and a portion of the endogenous RAMP1 or RAMP3 gene is deleted upon homologous recombination, an additional consideration is the size of the deleted portion of the endogenous RAMP1 or RAMP3 gene. If this portion of the endogenous gene is greater than 1 Kb in length, then a targeting cassette with regions of homology that are longer than 1 Kb is recommended to enhance the efficiency of recombination. Further guidance regarding the selection and use of sequences effective for homologous recombination is described in the literature (see, e.g., Deng and Capecchi, Mol. Cell. Biol. 12: 3365–3371, 1992; Bollag et al., Annu. Rev. Genet. 23: 199–225, 1989; and Waldman and Liskay, Mol. Cell. Biol. 8: 5350–5357, 1988).

A wide variety of cloning vectors may be used as vector backbones in the construction of the RAMP1 or RAMP3 gene targeting vectors of the present invention, including pBluescript-related plasmids (e.g., Bluescript KS+11), pQE70, pQE60, pQE-9, pBS, pD10, phagescript, phiX174, pBK Phagemid, pNH8A, pNH16a, pNH18Z, pNH46A, ptrc99a, pKK223-3, pKK233-3, pDR540, and pRIT5 PWLNEO, pSV2CAT, pXT1, pSG, pSVK3, PBPV, PMSG, and pSVL, pBR322 and pBR322-based vectors, pBM9, pBR325, pKH47, pBR328, pHC79, phage Charon 28, pKB11, pKSV-10, pK19 related plasmids, pUC plasmids and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mass.). However, any other vectors, e.g. plasmids, viruses, or parts thereof, may be used as long as they are replicable and viable in the desired host. The vector may also comprise sequences which enable it to replicate in the host whose genome is to be modified. The use of such a vector can expand the interaction period during which recombination can occur, increasing the efficiency of targeting (see Molecular Biology, ed. Ausubel et al, Unit 9.16, FIG. 9.16.1).

The specific host employed for propagating the targeting vectors of the present invention is not critical. Examples include E. coli K12 RR1 (Bolivar et al., Gene 2: 95, 1977), E. coli K12 HB101 (ATCC No. 33694), E. coli MM21 (ATCC No. 336780), E. coli DH1 (ATCC No. 33849), E. coli strain DH5α, and E coli STBL2. Alternatively, hosts such as S. cerevisiae or B. subtilis can be used. The above-mentioned hosts are available commercially (e.g. Stratagene, La Jolla, Calif.; and Life Technologies, Rockville, Md.).

To create the targeting vector, a RAMP1 or RAMP3 gene targeting construct is added to an above-described vector backbone. The RAMP gene targeting constructs of the invention have at least one RAMP gene homology region. To make the gene homology regions, a RAMP1 or RAMP3 gene sequence is used as a basis for producing polymerase chain reaction (PCR) primers. These primers are used to amplify the desired region of a RAMP genomic or cDNA sequence by high fidelity PCR amplification (Mattila et al., Nucleic Acids Res. 19: 4967, 1991; Eckert and Kunkel 1: 17, 1991; and U.S. Pat. No. 4,683, 202). The genomic sequence is obtained from a clone library or a preparation of genomic DNA or cDNA, preferably from the animal species that is to be targeted for RAMP gene disruption. The coding sequences for human and mouse RAMP1 are disclosed in GenBank accession numbers AJ001014 and BAA76617, respectively; the coding sequences for human and mouse RAMP3 are disclosed in GenBank accession numbers AJ001016 and AAD35020, respectively.

Preferably, the targeting constructs of the invention also include an exogenous nucleotide sequence encoding a positive marker protein. The stable expression of a positive marker after vector integration confers an identifiable characteristic on the cell without compromising cell viability. Therefore, in the case of a replacement vector, the marker gene is positioned between two flanking homology regions so that it integrates into the RAMP1 or RAMP3 gene following the double crossover event.

It is preferred that the positive marker protein is a selectable protein; the stable expression of such a protein in a cell confers a selectable phenotypic characteristic, i.e., the characteristic enhances the survival of the cell under otherwise lethal conditions. Thus, by imposing the selectable condition, one can isolate cells that stably express the positive selectable marker-encoding vector sequence from other cells that have not successfully integrated the vector sequence on the basis of viability. Examples of positive selectable marker proteins (and their agents of selection) include Neo (G418 or kanamycin kinase), Hyg (hygromycin), HisD (histidinol), Gpt (xanthine), Ble (bleomycin), and Hprt (hypoxanthine) (see, e.g., Capecchi and Thomas, U.S. Pat. No. 5,464,764, and Capecchi, Science 244: 1288–92, 1989). Other positive markers that may also be used as an alternative to a selectable marker include reporter proteins such as β-galactosidase, firefly luciferase, or green fluorescent protein (see, e.g., Current Protocols in Cytometry, Unit 9.5, and Current Protocols in Molecular Biology, Unit 9.6, John Wiley & Sons, New York, N.Y., 2000).

The above-described positive selection step does not distinguish between cells that have integrated the vector by targeted homologous recombination at the RAMP1 or RAMP3 gene locus versus random, non-homologous integration of vector sequence into any chromosomal position. Therefore, when using a replacement vector for homologous recombination, it is also preferred to include a nucleotide sequence encoding a negative selectable marker protein. Expression of a negative selectable marker causes a cell expressing the marker to lose viability when exposed to a certain agent (i.e., the marker protein becomes lethal to the cell under certain selectable conditions). Examples of negative selectable markers (and their agents of lethality) include herpes simplex virus thymidine kinase (gancyclovir or 1,2-deoxy-2-fluoro-α-d-arabinofuransyl-5-iodouracil), Hprt (6-thioguanine or 6-thioxanthine), and diphtheria toxin, ricin toxin, or cytosine deaminase (5-fluorocytosine).

The nucleotide sequence encoding the negative selectable marker is positioned outside of the two homology regions of the replacement vector. Given this positioning, cells will only integrate and stably express the negative selectable marker if integration occurs by random, non-homologous recombination; homologous recombination between the RAMP1 or RAMP3 gene and the two regions of homology in the targeting construct excludes the sequence encoding the negative selectable marker from integration. Thus, by imposing the negative condition, cells that have integrated the targeting vector by random, non-homologous recombination lose viability.

A combination of positive and negative selectable markers is a preferred selection scheme for making the genetically-modified non-human mammals and animal cells of the invention because a series of positive and negative selection steps can be designed to select only those cells that have undergone vector integration by homologous recombination, and, therefore, have a potentially disrupted RAMP1 or RAMP3 gene. Further examples of positive-negative selection schemes, selectable markers, and targeting constructs are described, for example, in U.S. Pat. No. 5,464,764, WO 94/06908, and Valancius and Smithies, Mol. Cell. Biol. 11: 1402, 1991.

In order for a marker protein to be stably expressed upon vector integration, the targeting vector may be designed so that the marker coding sequence is operably linked to the endogenous RAMP1 or RAMP3 gene promoter upon vector integration. Expression of the marker is then driven by the endogenous gene promoter in cells that normally express the RAMP1 or RAMP3 gene. Alternatively, each marker in the targeting construct of the vector may contain its own promoter that drives expression independent of the RAMP1 or RAMP3 gene promoter. This latter scheme has the advantage of allowing for expression of markers in cells that do not typically express the RAMP1 or RAMP3 gene (Smith and Berg, Cold Spring Harbor Symp. Quant. Biol. 49: 171, 1984; Sedivy and Sharp, Proc. Natl. Acad. Sci. (USA) 86: 227:1989; Thomas and Capecchi, Cell 51: 503, 1987).

Exogenous promoters that can be used to drive marker gene expression include cell-specific or stage-specific promoters, constitutive promoters, and inducible or regulatable promoters. Examples of these promoters include the herpes simplex thymidine kinase promoter, cytomegalovirus (CMV) promoter/enhancer, SV40 promoters, PGK promoter, PMC1-neo, metallothionein promoter, adenovirus late promoter, vaccinia virus 7.5K promoter, avian beta globin promoter, histone promoters (e.g., mouse histone H3-614), beta actin promoter, neuron-specific enolase, muscle actin promoter, and the cauliflower mosaic virus 35S promoter (see, generally, Sambrook et al., *Molecular Cloning*, Vols. I–III, Cold Spring Harbor Laboratory Press, Cold Spring Harbor, N.Y., 1989, and *Current Protocols in Molecular Biology*, John Wiley & Sons, New York, N.Y., 2000; Stratagene, La Jolla, Calif.).

To confirm whether cells have integrated the vector sequence into the targeted gene locus, primers or genomic probes that are specific for the desired vector integration event can be used in combination with PCR or Southern blot analysis to identify the presence of the desired vector integration into the RAMP1 or RAMP3 gene locus (Erlich et al., Science 252: 1643–51, 1991; Zimmer and Gruss, Nature 338: 150, 1989; Mouellic et al., Proc. Natl. Acad. Sci. (USA) 87: 4712, 1990; and Shesely et al., Proc. Nat. Acad. Sci. (USA) 88: 4294, 1991).

2. Gene Trapping

Another method available for inserting a foreign nucleic acid sequence into the RAMP1, RAMP2, or RAMP3 gene locus to disrupt the gene is gene trapping. This method takes advantage of the cellular machinery present in all mammalian cells that splices exons into mRNA to insert a gene trap vector coding sequence into a gene in a random fashion. Once inserted, the gene trap vector creates a mutation that may disrupt the trapped RAMP gene. In contrast to homologous recombination, this system for mutagenesis creates largely random mutations. Thus, to obtain a genetically-modified cell that contains a disrupted RAMP gene, cells containing this particular mutation must be identified and selected from a pool of cells that contain random mutations in a variety of genes.

Gene trapping systems and vectors have been described for use in genetically modifying murine cells and other cell types (see, e.g., Allen et al., Nature 333: 852–55, 1988; Bellen et al., Genes Dev. 3: 1288–1300, 1989; Bier et al., Genes Dev. 3: 1273–1287, 1989; Bonnerot et al., J. Virol. 66: 4982–91, 1992; Brenner et al., Proc. Nat. Acad. Sci. USA 86: 5517–21, 1989; Chang et al., Virology 193: 737–47, 1993; Friedrich and Soriano, Methods Enzymol. 225: 681–701, 1993; Friedrich and Soriano, Genes Dev. 5: 1513–23, 1991; Goff, Methods Enzymol. 152: 469–81, 1987; Gossler et al., Science 244: 463–65, 1989; Hope, Develop. 113: 399–408, 1991; Kerretal., Cold Spring Harb. Symp. Quant. Biol. 2: 767–776, 1989; Reddy et al., J. Virol. 65: 1507–1515, 1991; Reddy et al., Proc. Natl. Acad. Sci. U.S.A. 89: 6721–25, 1992; Skarnes et al., Genes Dev. 6: 903–918, 1992; von Melchner and Ruley, J. Virol. 63: 3227–3233, 1989; and Yoshida et al., Transgen. Res. 4: 277–87, 1995).

Promoter trap, or 5', vectors contain, in 5' to 3' order, a splice acceptor sequence followed by an exon, which is typically characterized by a translation initiation codon and open reading frame and/or an internal ribosome entry site. In general, these promoter trap vectors do not contain promoters or operably linked splice donor sequences. Consequently, after integration into the cellular genome of the host cell, the promoter trap vector sequence intercepts the normal splicing of the upstream gene and acts as a terminal exon. Expression of the vector coding sequence is dependent upon the vector integrating into an intron of the disrupted gene in the proper reading frame. In such a case, the cellular splicing machinery splices exons from the trapped gene upstream of the vector coding sequence (Zambrowicz et al., WO 99/50426).

An alternative method for producing an effect similar to the above-described promoter trap vector is a vector that incorporates a nested set of stop codons present in, or otherwise engineered into, the region between the splice acceptor of the promoter trap vector and the translation initiation codon or polyadenylation sequence. The coding sequence can also be engineered to contain an independent ribosome entry site (IRES) so that the coding sequence will be expressed in a manner largely independent of the site of integration within the host cell genome. Typically, but not necessarily, an IRES is used in conjunction with a nested set of stop codons.

Another type of gene trapping scheme uses a 3' gene trap vector. This type of vector contains, in operative combination, a promoter region, which mediates expression of an adjoining coding sequence, the coding sequence, and a splice donor sequence that defines the 3' end of the coding sequence exon. After integration into a host cell genome, the transcript expressed by the vector promoter is spliced to a splice acceptor sequence from the trapped gene that is located downstream of the integrated gene trap vector sequence. Thus, the integration of the vector results in the expression of a fusion transcript comprising the coding sequence of the 3' gene trap cassette and any downstream cellular exons, including the terminal exon and its polyadenylation signal. When such vectors integrate into a gene, the cellular splicing machinery splices the vector coding sequence upstream of the 3' exons of the trapped gene. One advantage of such vectors is that the expression of the 3' gene trap vectors is driven by a promoter within the gene trap cassette and does not require integration into a gene that is normally expressed in the host cell (Zambrowicz et al., WO 99/50426). Examples of transcriptional promoters and enhancers that may be incorporated into the 3' gene trap vector include those discussed above with respect to targeting vectors.

The viral vector backbone used as the structural component for the promoter or 3' gene trap vector may be selected from a wide range of vectors that can be inserted into the genome of a target cell. Suitable backbone vectors include, but are not limited to, herpes simplex virus vectors, adenovirus vectors, adeno-associated virus vectors, retroviral vectors, lentiviral vectors, pseudorabies virus vectors, alphaherpes virus vectors, and the like. A thorough review of viral vectors, in particular, viral vectors suitable for modifying nonreplicating cells and how to use such vectors in conjunction with the expression of an exogenous polynucleotide sequence, can be found in *Viral Vectors: Gene Therapy and Neuroscience Applications,* Eds. Caplitt and Loewy, Academic Press, San Diego, 1995.

Preferably, retroviral vectors are used for gene trapping. These vectors can be used in conjunction with retroviral packaging cell lines such as those described in U.S. Pat. No. 5,449,614. Where non-murine mammalian cells are used as target cells for genetic modification, amphotropic or pantropic packaging cell lines can be used to package suitable vectors (Ory et al., Proc. Natl. Acad. Sci., USA 93: 11400–11406, 1996). Representative retroviral vectors that can be adapted to create the presently described gene trap vectors are described, for example, in U.S. Pat. No. 5,521,076.

The gene trapping vectors may contain one or more of the positive marker genes discussed above with respect to targeting vectors used for homologous recombination. Similar to their use in targeting vectors, these positive markers are used in gene trapping vectors to identify and select cells that have integrated the vector into the cell genome. The marker gene may be engineered to contain an IRES so that the marker will be expressed in a manner largely independent of the location in which the vector has integrated into the target cell genome.

Given that gene trap vectors will integrate into the genome of infected host cells in a fairly random manner, a genetically-modified cell having a disrupted RAMP1, RAMP2, or RAMP3 gene must be identified from a population of cells that have undergone random vector integration. Preferably, the genetic modifications in the population of cells are of sufficient randomness and frequency such that the population represents mutations in essentially every gene found in the cell's genome, making it likely that a cell with the desired disrupted RAMP gene will be identified from the population (see Zambrowicz et al., WO 99/50426; Sands et al., WO 98/14614).

Individual mutant cell lines containing a disrupted RAMP1, RAMP2, or RAMP3 gene are identified in a population of mutated cells using, for example, reverse transcription and PCR to identify a mutation in the gene sequence. This process can be streamlined by pooling clones. For example, to find an individual clone containing a disrupted RAMP gene, RT-PCR is performed using one primer anchored in the gene trap vector and the other primer located in the RAMP gene sequence. A positive RT-PCR result indicates that the vector sequence is encoded in the RAMP gene transcript, indicating that the RAMP gene has been disrupted by a gene trap integration event (see, e.g., Sands et al., WO 98/14614).

Temporal, Spatial, and Inducible RAMP Gene Disruptions

In certain embodiments of the present invention, a functional disruption of the endogenous RAMP1, RAMP2, or RAMP3 gene occurs at specific developmental or cell cycle stages (temporal disruption) or in specific cell types (spatial disruption). In other embodiments, the gene disruption is inducible. The Cre-Lox system may be used to activate or inactivate the RAMP gene at a specific developmental stage, in a particular tissue or cell type, or under particular environmental conditions. Generally, methods utilizing Cre-Lox technology are carried out as described by Torres and Kuhn, *Laboratory Protocols for Conditional Gene Targeting,* Oxford University Press, 1997. Methodology similar to that described for the Cre-Lox system can also be employed utilizing the FLP-FRT system. The FLP-FRT system and further guidance regarding the use of recombinase excision systems for conditionally disrupting genes by homologous recombination or viral insertion are provided in the literature (see, e.g., U.S. Pat. Nos. 5,626,159, 5,527,695, 5,434,066, Gaitanaris, WO 98/29533, Orban et al., Proc. Nat. Acad. Sci. USA 89: 6861–65, 1992; O'Gorman et al., Science 251: 1351–55, 1991; Sauer et al., Nucleic Acids Research 17: 147–61, 1989; Barinaga, Science 265: 26–28, 1994; and Akagi et al., Nucleic Acids Res. 25: 1766–73, 1997). More than one recombinase system can be used to genetically modify an animal or cell.

When using homologous recombination to disrupt the desired RAMP gene in a temporal, spatial, or inducible fashion, using a recombinase system such as the Cre-Lox system, a portion of the RAMP1, RAMP2, or RAMP3 gene coding region is replaced by a targeting construct comprising the RAMP gene coding region flanked by loxP sites. Non-human mammals and animal cells carrying this genetic modification contain a functional, loxP-flanked RAMP gene.

The temporal, spatial, or inducible aspect of the RAMP gene disruption is caused by the expression pattern of an additional transgene, a Cre recombinase transgene, that is expressed in the non-human mammal or animal cell under the control of the desired spatially-regulated, temporally-regulated, or inducible promoter, respectively. A Cre recombinase targets the loxP sites for recombination. Therefore, when Cre expression is activated, the LoxP sites undergo recombination to excise the sandwiched RAMP gene coding sequence, resulting in a functional disruption of the RAMP gene (Rajewski et al., J. Clin. Invest. 98: 600–03, 1996; St.-Onge et al., Nucleic Acids Res. 24: 3875–77, 1996; Agah et al., J. Clin. Invest. 100: 169–79, 1997; Brocard et al., Proc. Natl. Acad. Sci. USA 94: 14559–63, 1997; Feil et al., Proc. Natl. Acad. Sci. USA 93: 10887–90, 1996; and Kühn et al., Science 269: 1427–29, 1995).

A cell containing both a Cre recombinase transgene and loxP-flanked RAMP gene can be generated through standard transgenic techniques or, in the case of genetically-modified, non-human mammals, by crossing genetically-modified, non-human mammals wherein one parent contains a loxP flanked RAMP gene and the other contains a Cre recombinase transgene under the control of the desired promoter. Further guidance regarding recombinase systems and specific promoters useful to conditionally disrupt a RAMP gene is found, for example, in Sauer, Meth. Enz. 225: 890–900, 1993, Gu et al., Science 265: 103–06, 1994, Araki et al., J. Biochem. 122: 977–82, 1997, Dymecki, Proc. Natl. Acad. Sci. 93: 6191–96, 1996, and Meyers et al., Nature Genetics 18: 136–41, 1998.

An inducible disruption of the RAMP1, RAMP2, or RAMP3 gene can also be achieved by using a tetracycline responsive binary system (Gossen and Bujard, Proc. Natl. Acad. Sci. USA 89: 5547–51, 1992). This system involves genetically modifying a cell to introduce a Tet promoter into the endogenous RAMP1, RAMP2, or RAMP3 gene regulatory element and a transgene expressing a tetracycline-controllable repressor (TetR). In such a cell, the administration of tetracycline activates the TetR which, in turn, inhibits the RAMP gene expression and, therefore, disrupts the RAMP gene (St.-Onge et al., Nucleic Acids Res. 24: 3875–77, 1996, U.S. Pat. No. 5,922,927).

Temporal, spatial, and inducible disruptions of a RAMP gene can also be made using gene trapping as the method of genetic modification, for example, as described in Gaitanaris et al. WO 98/29533.

Genetically-Modified, Non-human Mammals and Animal Cells

The above-described methods for genetic modification can be used to disrupt a RAMP1, RAMP2, or RAMP3 gene in virtually any type of somatic or stem cell derived from an animal. Genetically-modified animal cells of the invention include, but are not limited to, mammalian cells, including human cells, and avian cells. These cells may be derived from genetically engineering any animal cell line, such as culture-adapted, tumorigenic, or transformed cell lines, or they may be isolated from a genetically-modified, non-human mammal carrying the desired genetic modification to the RAMP gene.

The cells may be heterozygous (+/−) or homozygous (−/−) for a RAMP gene disruption. To obtain cells that are homozygous for the RAMP gene disruption, direct, sequential targeting of both alleles can be performed. This process can be facilitated by recycling a positive selectable marker. According to this scheme the nucleotide sequence encoding the positive selectable marker is removed following the disruption of one RAMP1, RAMP2, or RAMP3 allele using the Cre-Lox P system. Thus, the same vector can be used in a subsequent round of targeting to disrupt the second respective RAMP1, RAMP2, or RAMP3 gene allele (Abuin and Bradley, Mol. Cell. Biol. 16: 1851–56, 1996; Sedivy et al., T.I.G. 15: 88–90, 1999; Cruz et al., Proc. Natl. Acad. Sci. (USA) 88: 7170–74, 1991; Mortensen et al., Proc. Natl. Acad. Sci. (USA) 88: 7036–40,1991; te Riele et al., Nature (London) 348: 649–651, 1990).

An alternative strategy for obtaining ES cells that are homozygous for a RAMP gene disruption is the homogenotization of cells from a population of cells that are heterozygous for the RAMP disruption. The method uses a scheme in which heterozygote targeted clones that express a selectable drug resistance marker are selected against a very high drug concentration; this selection favors cells that express two copies of the sequence encoding the drug resistance marker and are, therefore, homozygous for the RAMP gene disruption (Mortensen et al., Mol. Cell. Biol. 12: 2391–95, 1992). In addition, genetically-modified animal cells that are homozygous for a RAMP1 or RAMP3 gene disruption can be obtained from genetically-modified RAMP1−/− or RAMP3−/− non-human mammals that are created by mating RAMP1 +/− or RAMP3+/− heterozygotes, as further discussed below.

Following the genetic modification of the desired cell or cell line, the RAMP1, RAMP2, or RAMP3 gene locus can be confirmed as the site of modification by PCR analysis according to standard PCR or Southern blotting methods known in the art (see, e.g., U.S. Pat. No. 4,683,202; and Erlich et al., Science 252: 1643, 1991). Further verification that the genetic modification disrupts the desired RAMP gene may also be made if RAMP1, RAMP2, or RAMP3 gene mRNA levels and/or polypeptide levels are reduced in cells that normally express the RAMP gene. Measures of RAMP gene mRNA levels may be obtained by using reverse transcriptase mediated PCR (RT-PCR), Northern blot analysis, or in situ hybridization. The quantification of RAMP polypeptide levels produced by the cells can be made, for example, by standard immunoassay methods known in the art. Such immunoassays include, but are not limited to, competitive and non-competitive assay systems using techniques such as radioimmunoassays, ELISA (enzyme-linked immunosorbent assay), "sandwich" immunoassays, immunoradiometric assays, gel diffusion precipitin reactions, immunodiffusion assays, in situ immunoassays (using colloidal gold, enzymatic, or radioisotope labels, for example), Western blots, precipitation reactions, immunofluorescence assays, protein A assays, and immunoelectrophoresis assays.

Preferred genetically-modified animal cells are ES cells and ES-like cells. These cells are derived from the preimplantation embryos and blastocysts of various species, such as mice (Evans et al., Nature 129:154–156, 1981; Martin, Proc. Natl. Acad. Sci., USA, 78: 7634–7638, 1981), pigs and sheep (Notanianni et al., J. Reprod. Fert. Suppl., 43: 255–260, 1991; Campbell et al., Nature 380: 64–68,1996) and primates, including humans (Thomson et al., U.S. Pat. No. 5,843,780, Thomson et al., Science 282: 1145–1147, 1995; and Thomson et al., Proc. Natl. Acad. Sci. USA 92: 7844–7848, 1995).

These types of cells are pluripotent. That is, under proper conditions, they differentiate into a wide variety of cell types derived from all three embryonic germ layers: ectoderm, mesoderm and endoderm. Depending upon the culture conditions, a sample of ES cells can be cultured indefinitely as stem cells, allowed to differentiate into a wide variety of different cell types within a single sample, or directed to differentiate into a specific cell type, such as macrophage-like cells, hepatocytes, pancreatic β-cells, neuronal cells, cardiomyocytes, chondrocytes, adipocytes, smooth muscle cells, endothelial cells, skeletal muscle cells, keratinocytes, and hematopoietic cells, such as eosinophils, mast cells, erythroid progenitor cells, or megakaryocytes. Directed differentiation is accomplished by including specific growth factors or matrix components in the culture conditions, as further described, for example, in Keller et al., Curr. Opin. Cell Biol. 7:862–69, 1995, Li et al., Curr. Biol. 8: 971, 1998, Klug et al., J. Clin. Invest. 98: 216–24, 1996, Lieschke et al., Exp. Hematol. 23: 328–34, 1995, Yamane et al., Blood 90: 3516–23, 1997, and Hirashima et al., Blood 93: 1253–63, 1999.

Genetically-modified murine ES cells may be used to generate genetically-modified mice. Embryonic stem cells are manipulated according to published procedures (Robertson, 1987, *Teratocarcinomas and Embryonic Stem Cells: A Practical Approach,* Ed. E. J. Robertson, Oxford: IRL Press, pp. 71–112, 1987; Zjilstra et al., Nature 342: 435–438, 1989; and Schwartzberg et al., Science 246: 799–803, 1989). The particular embryonic stem cell line employed is not critical; exemplary murine ES cell lines include AB-1 (McMahon and Bradley, Cell 62:1073–85, 1990), E14 (Hooper et al., Nature 326: 292–95, 1987), D3 (Doetschman et al., J. Embryol. Exp. Morph. 87: 27–45, 1985), CCE (Robertson et al, Nature 323: 445–48, 1986), RW4 (Genome Systems, St. Louis, Mo.), and DBA/1lacJ (Roach et al., Exp. Cell Res. 221: 520–25, 1995).

Following confirmation that the ES cells contain the desired functional disruption of the RAMP1, RAMP2, or RAMP3 gene, these ES cells are then injected into suitable blastocyst hosts for generation of chimeric mice according to methods known in the art (Capecchi, Trends Genet. 5: 70, 1989). The particular mouse blastocysts employed in the present invention are not critical. Examples of such blastocysts include those derived from C57BL/6 mice, C57BL/6 Albino mice, Swiss outbred mice, CFLP mice, and MFI mice. Alternatively, ES cells may be sandwiched between tetraploid embryos in aggregation wells (Nagy et al., Proc. Natl. Acad. Sci. USA 90: 8424–8428, 1993).

The blastocysts containing the genetically-modified ES cells are then implanted in pseudopregnant female mice and allowed to develop in utero (Hogan et al., *Manipulating the Mouse Embryo: A Laboratory Manual,* Cold Spring Harbor Laboratory, 1988; and *Teratocarcinomas and Embryonic Stem Cells: A Practical Approach,* E. J. Robertson, ed., IRL Press, Washington, D.C., 1987). The offspring born to the foster mothers may be screened to identify those that are chimeric for the RAMP1, RAMP2, or RAMP3 gene disruption. Such offspring contain some cells that are derived from the genetically-modified donor ES cell as well as other cells from the original blastocyst. Offspring may be screened initially for mosaic coat color where a coat color selection strategy has been employed to distinguish cells derived from the donor ES cell versus the other cells of the blastocyst. Alternatively, DNA from tail tissue of the offspring can be used to identify mice containing the genetically-modified cells.

The mating of chimeric mice that contain the RAMP1, RAMP2, or RAMP3 gene disruption in germ line cells produces progeny that possess the respective RAMP1 or RAMP3 gene disruption in all germ line cells and somatic cells. Mice that are heterozygous for either the RAMP1 or RAMP3 gene disruption can then be crossed to produce homozygotes (see, e.g., U.S. Pat. Nos. 5,557,032, and 5,532, 158).

An alternative to the above-described ES cell technology for transferring a genetic modification from a cell to a whole animal is to use nuclear transfer. This method is not limited to making mice; it can be employed to make other genetically-modified, non-human mammals, for example, sheep (McCreath et al., Nature 29: 1066–69, 2000; Campbell et al., Nature 389: 64–66, 1996; and Schnieke et al., Science 278: 2130–33, 1997) and calves (Cibelli et al., Science 280: 1256–58, 1998). Briefly, somatic cells (e.g., fibroblasts) or pluripotent stem cells (e.g., ES-like cells) are selected as nuclear donors and are genetically-modified to contain a functional disruption of the RAMP1, RAMP2, or RAMP3 gene. When inserting a DNA vector into a somatic cell to mutate the desired RAMP gene, it is preferred that a promoterless marker be used in the vector such that vector integration into the RAMP gene results in expression of the marker under the control of the promoter of the disrupted RAMP gene (Sedivy and Dutriaux, T. I. G. 15: 88–90, 1999; McCreath et al., Nature 29: 1066–69, 2000). Nuclei from donor cells which have the appropriate RAMP gene disruption are then transferred to fertilized or parthenogenetic oocytes that are enucleated (Campbell et al., Nature 380: 64, 1996; Wilmut et al., Nature 385: 810, 1997). Embryos are reconstructed, cultured to develop into the morula/blastocyst stage, and transferred into foster mothers for in utero full term development.

The present invention also encompasses the progeny of the genetically-modified, non-human mammals and genetically-modified animal cells. While the progeny are heterozygous or homozygous for the genetic modification that disrupts the RAMP gene, they may not be genetically identical to the parent non-human mammals and animal cells due to mutations or environmental influences that may occur in succeeding generations at other loci besides that of the original RAMP gene disruption described herein.

"Humanized" Non-human Mammals and Animal Cells

The genetically-modified non-human mammals and animal cells (non-human) of the invention, containing a disrupted endogenous RAMP1, RAMP2, or RAMP3 gene, can be further modified to express a corresponding human RAMP1, RAMP2, or RAMP3 sequence (referred to herein as "humanized"). The human RAMP1, RAMP2, and RAMP3 gene coding sequences are disclosed, for example, in GenBank Accession Nos. AJ001014, AJ001015, and AJ001016, respectively.

A preferred method for humanizing cells involves replacing the endogenous RAMP sequence with a nucleic acid sequence encoding the corresponding human RAMP sequence by homologous recombination. The targeting vectors are similar to those traditionally used as knock out vectors with respect to the 5' and 3' homology arms and positive/negative selection schemes. However, the vectors also include sequence that, after recombination, either substitutes the human coding sequence for the endogenous sequence, or effects base pair changes, exon substitutions, or codon substitutions that modify the endogenous sequence to encode the human RAMP sequence. Once homologous recombinants have been identified, it is possible to excise any selection-based sequences (e.g., Neo) by using Cre or Flp-mediated site directed recombination (Dymecki, Proc. Natl. Acad. Sci. 93: 6191–96, 1996).

When substituting the human RAMP1, RAMP2, or RAMP3 sequence for the corresponding endogenous sequence, it is preferred that these changes are introduced directly downstream of the endogenous translation start site. This positioning preserves the endogenous temporal and spatial expression patterns of the RAMP gene. The human sequence can be the full length human cDNA sequence with a polyA tail attached at the 3' end for proper processing or the whole genomic sequence (Shiao et al., Transgenic Res. 8: 295–302, 1999). Further guidance regarding these methods of genetically modifying cells and non-human mammals to replace expression of an endogenous gene with its human counterpart is found, for example, in Sullivan et al., J. Biol. Chem. 272: 17972–80, 1997, Reaume et al., J. Biol. Chem. 271: 23380–88, 1996, and Scott et al., U.S. Pat. No. 5,777, 194).

Another method for creating such "humanized" organisms is a two step process involving the disruption of the endogenous gene followed by the introduction of a transgene encoding the human sequence by pronuclear microinjection into the knock-out embryos.

EXAMPLE 1

Generation of Genetically-Modified Mice of the Following Genotypes:

RAMP1 +/−, RAMP1−/−, RAMP2+/− RAMP3+/−, and RAMP3−/−

The genetically-modified mouse ES cells and mice carrying a targeted disruption in the RAMP1, RAMP2 or RAMP3 gene were generated using homologous recombination (DeltaGen, Menlo Park, Calif.).

For RAMP1 targeted disruption, a partial RAMP1 sequence, as shown in FIG. 1 (SEQ ID NO:1), was used to design a targeting construct. The exon sequence targeted for deletion and replacement with LacZ-Neo is shown as the double underlined sequence. A targeting construct was created, as shown in FIG. 2, which contained two homology arms (each of 10 nucleotides in length) of SEQ ID NOs: 2 and 3, and an IRES LacZ-Neo sequence.

Figure 3:
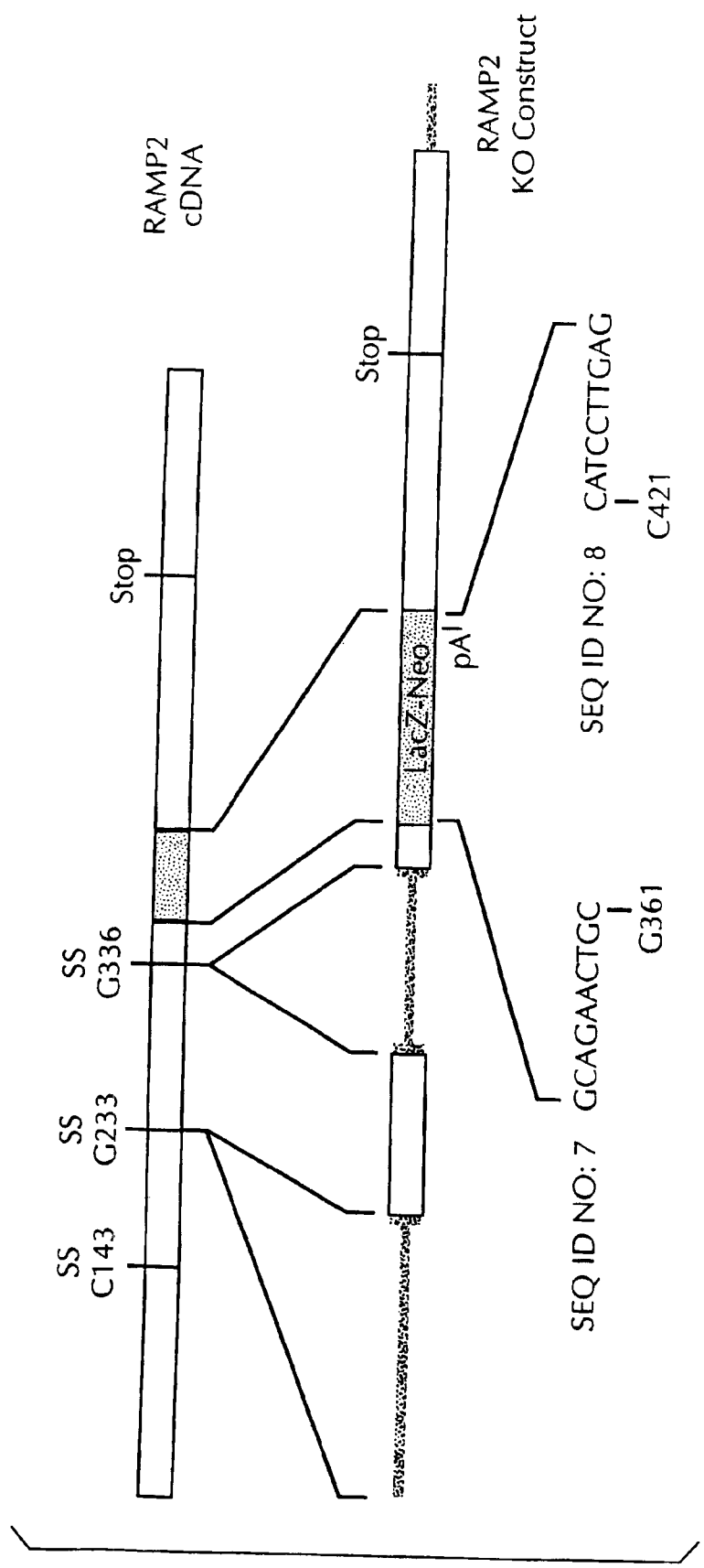
FIG. 3 is a schematic representation of the targeting construct used for homologous recombination with, and the disruption of, the RAMP2 gene. The region "X" represents the endogenous coding sequence targeted for deletion and replacement with LacZ-Neo. SS refers to splice sites. Numbers following nucleotide letters refer to the nucleotide position in the original mouse cDNA (top). pA in the targeting (KO) construct (bottom) refers to a polyadenylation signal used to truncate transcripts. SEQ ID NOs: 7 and 8 designate the sequences used as homology arms in the targeting construct.

For RAMP2 targeted disruption, a construct was creased as shown in FIG. 3, which contained two homology arms of SEQ ID NOs: 7 and 8 and an IRES-LacZ Neo sequence.

Figure 5:
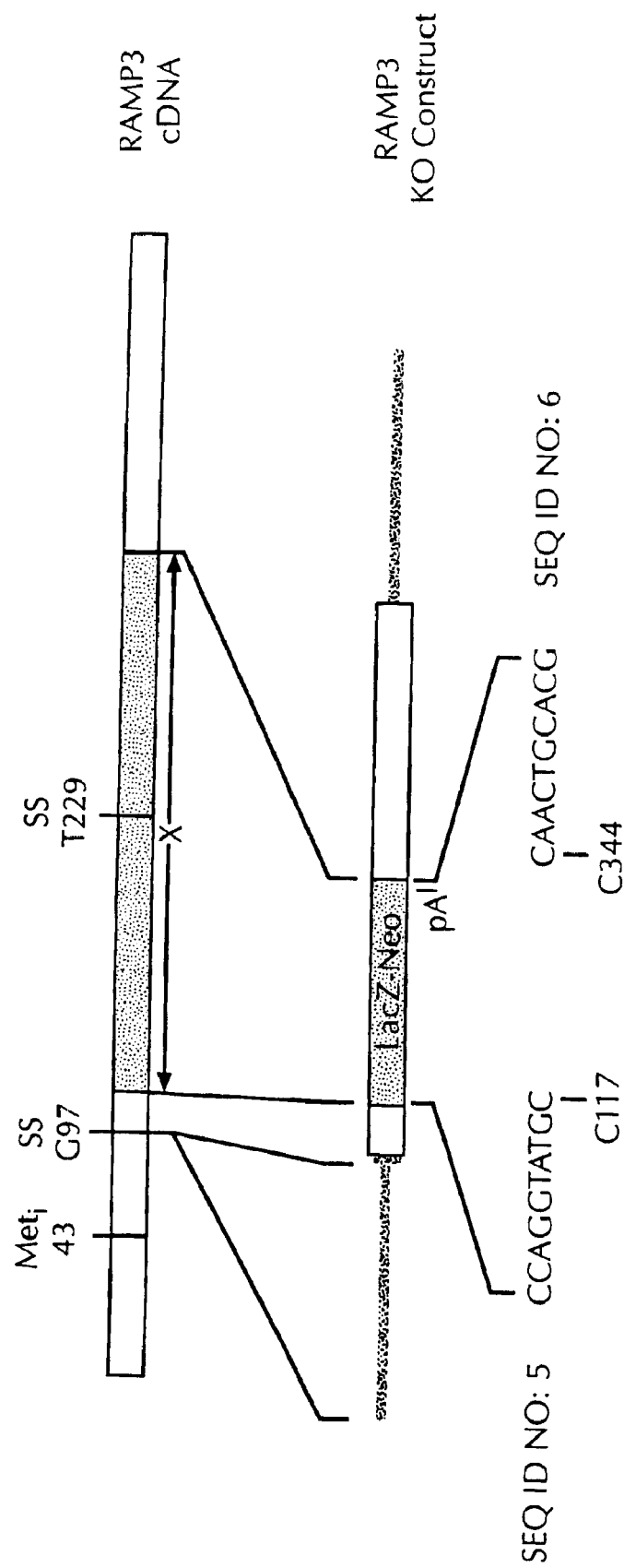
FIG. 5 is a schematic representation of the targeting construct used for homologous recombination with, and the disruption of, the murine RAMP3 gene. Numbers following nucleotide letters refer to the nucleotide position in the original mouse cDNA (top). The region "X" represents the region of the endogenous coding sequence targeted for deletion and replacement with LacZ-Neo. SS refers to putative splice sites. pA in the targeting (KO) construct (bottom) refers to a polyadenylation signal used to truncate transcripts. SEQ ID NOs: 5 and 6 designate the sequences used as homology arms in the targeting construct.

For RAMP3 targeted disruption, a partial RAMP-3 sequence, as shown in FIG. 4 (SEQ ID NO: 4), was used to design the targeting construct. The exon and intron sequences deleted by homologous recombination and replaced by LacZ-Neo are shown as the double underlined sequence. A schematic of the RAMP3 targeting construct, containing two homology arms of SEQ ID NOs: 5 and 6, is illustrated in FIG. 5.

The Neo sequence used in the targeting constructs was derived from pGT-N28 (New England Biolabs, Beverly, Mass.), and contained a specifically-introduced base change from T to G at position 555 of the Neo open reading frame to enhance neomycin resistance. The IRES-lacZ sequence is further described, for example, in Deng et al., Dev. Biol. 212: 307–22, 1999.

Figure 6A:
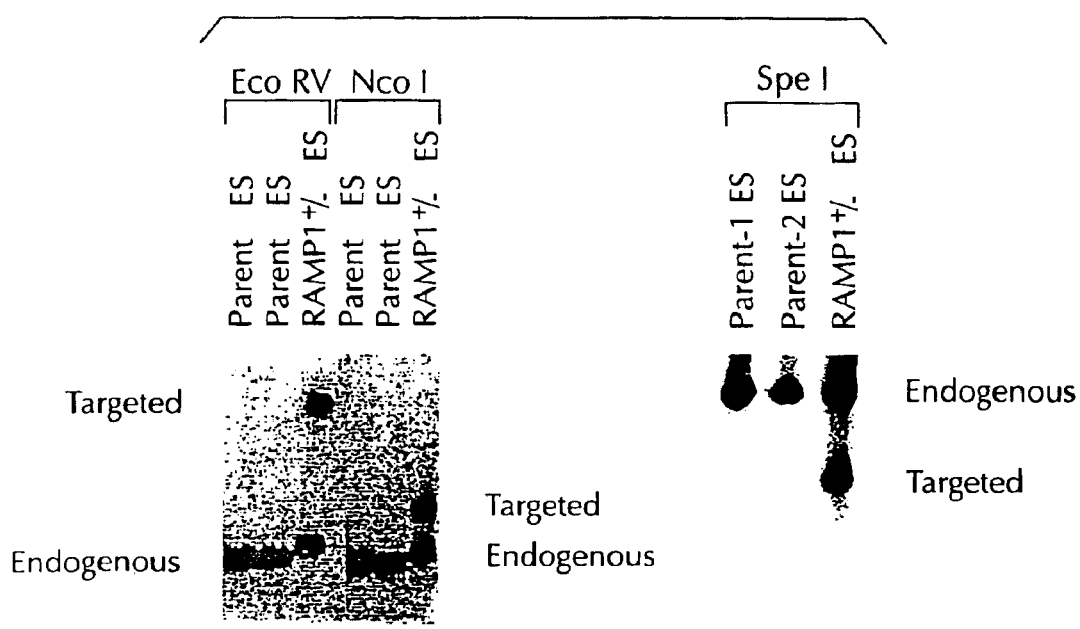
FIG. 6A depicts Southern blot confirmation of the targeted disruption of the RAMP1 gene in ES cell genomic DNA. The DNA was digested with restriction enzymes EcoRV, Ncol, or Spel, and the blot was hybridized to a radiolabeled DNA fragment designed to hybridize outside of and adjacent to a homology arm. The parent ES cell showed single bands representing the wild type RAMP allele. By contrast, the genetically modified ES cell (RAMP1+/−) demonstrated a second allele representing the targeted allele from the expected homologous recombination event.
Figure 6B:
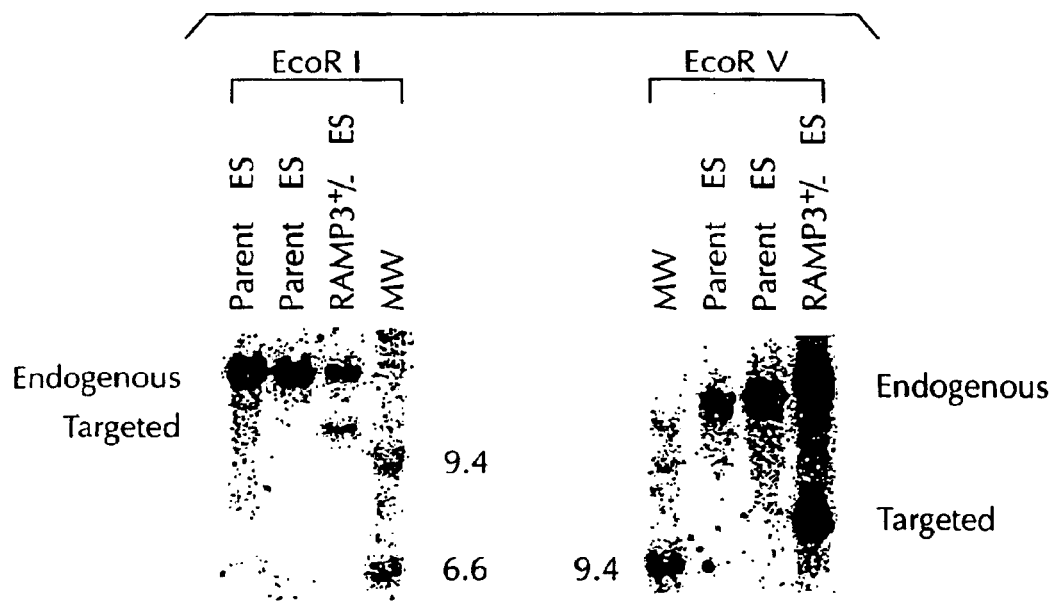
FIG. 6B depicts Southern blot confirmation of the targeted disruption of the RAMP3 gene. The parent ES cell showed single bands representing the wild type RAMP allele, whereas, the genetically modified ES cell (RAMP3+/−) demonstrated a second allele representing the targeted allele from the expected homologous recombination event. Genomic DNA was subjected to EcoRI or EcoRV digestion and blotted according to the protocol as described for FIG. 6A.

DNA containing the RAMP1, RAMP2, or RAMP3 targeting construct was inserted into ES R1 cells (Laboratory of Dr. Andras Nagy, as further described in Nagy et al., Proc. Natl. Acad. Sci. USA 90: 8424–28, 1993) by electroporation. ES cells that were neomycin resistant were analyzed by Southern blot to confirm the targeted disruption of the RAMP1, RAMP2, or RAMP3 gene. As shown in FIGS. 6A and 6B, Southern blot analysis of genomic DNA confirmed the homologous recombination event in the RAMP1 and RAMP3 genes, respectively.

The RAMP1, RAMP2, and RAMP3 targeted ES cells were then used, respectively, for generation of chimeric mice that were heterozygous for the RAMP1, RAMP2, or RAMP 3 targeted disruption by injecting the cells into C57BL/6 blastocysts (Harlan, Indianapolis, Ind.) and implanting the blastocysts into CD1 pseudopregnant mice (Charles River Laboratories, Wilmington, Mass.; see also, Capecchi et al., Trends Genet. 5: 70, 1989, Hogan et al., *Manipulating the Mouse Embryo: A Laboratory Manual*, Cold Spring Harbor Laboratory, 1988; and *Teratocarcinomas and Embryonic Stem Cells: A Practical Approach*, E. J. Robertson, ed., IRL Press, Washington, D.C., 1987). The chimeric mice were then bred with C57BL/6 (Charles River Laboratories) mice to create F1 heterozygotes. RAMP1 and RAMP3 heterozygotes were in turn bred to produce F2 homozygotic mice. The functional disruption of the RAMP1, RAMP2, and RAMP3 gene in the heterozygotes and homozygotes was confirmed by PCR and Southern blot analysis.

Characterization of the Function and Therapeutic Relevance of RAMPs

Genetically modifying a non-human mammal or animal cell to disrupt the RAMP1, RAMP2, or RAMP3 gene can be used to determine whether such disruption produces a physiologically relevant effect or phenotype. In non-human mammals homozygous for a RAMP1 or RAMP3 disruption, abnormal phenotypes associated with decreased RAMP1 or RAMP3 activity identify RAMP-associated functions and establish a basis for identifying and developing RAMP1-or RAMP3-targeted therapeutics for treating or preventing diseases or conditions associated with these functions. In addition, guidance for determining which cells, tissues, or phenotypes to study with respect to RAMP1, RAMP2, or RAMP3 function is found, for example, in the expression patterns for these proteins.

In addition, the RAMP1−/− and RAMP3−/− non-human mammals and animal cells are also useful to determine whether one RAMP plays a predominant role in vivo in cases where multiple RAMPs have redundant functions. For example, both RAMP1 and RAMP3 mediate amylin binding to the calcitonin receptor. Amylin administration in a mammal results in increased blood glucose and a decrease in glucose uptake by muscles. To determine whether these effects are caused predominantly by either RAMP 1 or RAMP3 action, amylin can be administered to wild type, RAMP1−/− and RAMP3−/− non-human mammals (e.g., mice or rats), or muscle preparations from such animals. If the RAMP1−/− mice have an amylin response similar to wild type mice, or if RAMP3−/− mice have a significantly different response, then the in vivo amylin response is predominantly mediated by the RAMP3 receptor. Conversely, if the RAMP3−/− mice have an amylin response similar to wild type mice, or if RAMP1−/− mice have a significantly impaired response, then the in vivo amylin response is predominantly mediated by RAMP1.

This above described approach can also be applied to determine if in vivo adrenomedulin signalling occurs predominantly through RAMP2 or RAMP3 action. Both RAMP2 and RAMP3 interact with the CRLR to mediate adrenomedullin signalling. Adrenomedullin causes vasodilation and a decrease in blood pressure. Therefore, to determine whether these physiological effects are caused primarily by RAMP2 or RAMP3 action, adrenomedullin can be administered to RAMP3−/− and wild type non-human mammals (e.g., mice or rats) or to a vascular strip preparation from such mammals. If the adrenomedullin response in the RAMP3−/− mammals are the same as the wild type, then normal signalling is predominantly through RAMP2. However, if the adrenomedullin response in the RAMP3−/− mice is significantly impaired, then RAMP3 normally plays a significant role in the physiological response to adrenomedullin.

1. RAMP1, RAMP2, and RAMP3 Expression

Our studies of RAMP1, RAMP2, and RAMP3 expression patterns, presented herein, are based upon expression of the reporter gene LacZ in RAMP1+/−, RAMP2+/−, and RAMP3+/− heterozygotic mice, respectively. Given that LacZ expression in these heterozygotic mice is controlled by the endogenous RAMP gene promoter, LacZ expression in these mice corresponds to the endogenous expression pattern of the targeted gene in wild type mice.

Tissue and organs from wild type and heterozygous mice (aged 6–8 weeks) were frozen, sectioned (10 μm), positioned on slides and fixed in 2% formaldehyde/0.2% glutaraldehyde for 1 min. The samples were washed for 1 min. in Tris buffer, pH 8.0, and submerged in a staining solution containing the β-galactosidase substrate X-gal (5-bromo-4-chloro-3-indoyl beta-D-galactosidase, Gold Biotechnology, St. Louis, Mo.) diluted in a ferricyanide buffer (Tissue Stain Base Solution, Specialty Media, Phillipsburg, N.J.) according to manufacturer's (Specialty Media, Phillipsburg, N.J.) recommendations. Following overnight incubation at room temperature, sections were rinsed in phosphate-buffered saline, topped with a coverslip, and photographed. The sections were counterstained with Nuclear Fast Red (Sigma-Aldrich, St. Louis, Mo.). The following tissues were excluded from the present expression study based upon staining in wild-type control samples due to endogenous β-galactosidase activity: small and large intestines, stomach, vas deferens and epididymus.

EXAMPLE 2

RAMP1 Expression

As described in McLatchie et al., Nature 393: 333–39, 1998, RAMP1 is expressed in heart, skeletal muscle, pancreas, brain, uterus, bladder, liver, and the gastrointestinal tract. The present results further delineate RAMP1 expression in brain, uterus, and liver, and identify additional tissues that express RAMP1 as well.

LacZ expression was observed throughout the brain, with extensive expression in the cerebrum, striatum, and in the second layer of the cortex. Other notable regions of brain expression included the piriform cortex, third ventricle, hippocampus, fourth ventricle, and brainstem. LacZ expression was also demonstrated in the male reproductive tract (e.g., the spermatogenetic and interstitial cells of the testis and the muscle layer surrounding the coagulating gland), the female reproductive tract (e.g., epithelial cells of the uterine (fallopian) tubules and in the follicular cells of the ovary), the liver (in the muscle layer of the central vein), in fibroblasts in the epithelium of the gallbladder, and in fibroblasts in the epidermis of the skin.

The RAMP1 expression patterns (as reported in Example 2 and/or in McLatchie et al) indicate that modulating RAMP1 activity in a mammal could affect pain sensation and cognitive enhancement (via RAMP1 expression in the striatum and the cerebral cortex); could be used to treat movement disorders such as Parkinson's disease, Huntington's disease and tremor (via RAMP1 expression in the dorsal striatum of the brain), psychosis, addiction, obsessive compulsive disorder, attention deficit disorder (via RAMP1 expression in the ventral striatum), psychosis, depression and anxiety (via RAMP1 activity expression in the piriform cortex); could improve memory impairment and Alzheimer's disease (via RAMP1 expression in the hippocampus), fertility and reproduction (via RAMP1 expression in the female or male reproductive tract); and could be used to treat or prevent the progression or occurrence, or the symptoms of the following diseases or conditions: dermatologic disorders (via RAMP1 expression in the skin), hepatocellular disorders (via RAMP1 expression in the central liver vein smooth muscle layer and in the gall bladder), disorders of muscle metabolism and/or glucose metabolism (via RAMP1 expression in the pancreas and skeletal muscle), cardiovascular disorders and/or hypertension (via RAMP1 expression in the heart).

EXAMPLE 3

RAMP2 Expression

RAMP2 expression was demonstrated in the spermatogenic cells of the testis, indicating that modulation of RAMP2 activity could be useful for the modulation of male fertility.

EXAMPLE 4

RAMP3 Expression

LacZ expression was demonstrated in the caudate putamen (striatum) and in the laterodorsal thalamic region of the cerebrum, and, diffusely, in the epithelial cells of the coagulating gland in the male reproductive tract.

The RAMP3 expression pattern in the caudate putamen of the brain indicates that modulating RAMP 3 activity in a mammal could be useful for treatment of movement disorders including Parkinson's disease, Huntington's disease, and tremor. RAMP3 expression in the coagulating gland indicates that modulating RAMP 3 activity in a mammal could be useful for treatment of sexual/reproductive disorders and benign prostatic hypertrophy.

2. Phenotypic Characterization

At ages of 6–8 weeks, mice homozygous for a RAMP1 or RAMP3 targeted disruption were phenotypically compared to appropriately-matched wild type controls. No mice homozygous for a RAMP2 targeted disruption were born. Data was collected from the RAMP1−/− and RAMP3−/− physical examination, necropsy, histology, clinical chemistry, blood chemistry, body length, body weight, organ weight, hematology, and the cytological evaluation of bone marrow (Deltagen, Menlo Park, Calif.).

EXAMPLE 5

RAMP1−/− and RAMP3−/− Mice Phenotypes

The role of RAMP1 in liver and muscle function, as discussed in Example 2, is further supported by the phenotypic characterization of RAMP1−/− mice. Elevations in the enzymatic activity of alanine aminotransferase (ALT), aspartate aminotransferase (AST) and creatine kinase (CK), indicators of heart, skeletal muscle, smooth muscle and/or liver cell damage, were detected in the RAMP1 −/− mice as indicated in Table 1.

TABLE 1

| Enzyme (IU/ml) | +/+ male | +/+ female | –/– male | –/– female |
|---|---|---|---|---|
| ALT | 22.5 ± 6.4 (2) | 16.5 ± 6.4 (2) | 21.7 ± 6.4 (3) | 133.3 ± 97.9 (3) |
| AST | 71 ± 15 (2) | 47 ± 2 (2) | 88 ± 59 (3) | 425 ± 290 (3) |
| CK | 363 ± 59 (2) | 200 ± 100 (2) | 11958 ± 9641 (3) | 609 ± 439 (3) |

Values are presented as the mean ± standard deviation (number of samples). Wild type mice are designated +/+; RAMP1–/– mice are designated –/–.

The results in Table 1 regarding muscle and liver cell damage indicate that modulating RAMP1 to increase activity would be useful in treating or preventing cardiovascular disorders such as congestive heart failure, acute myocardial infarction, skeletal muscle myopathies and hepatic diseases including chronic and acute hepatitis, hepatomegaly, hepatic steatosis, biliary atresia, gallstones, and chemical or drug-induced hepatotoxicity.

Examination of RAMP3–/– mice revealed no abnormal phenotypes.

Identification of Agents that Modulate RAMP Activity

To determine whether an agent modulates RAMP1, RAMP2, or RAMP3 activity, cells, tissue preparations, or whole animals, that express a RAMP gene can be used. It is preferred to use tissue or cell samples that express the human gene, such as those derived from human cell lines or from a primary human tissue preparation. Alternatively, such tissue or cell samples may be obtained from a humanized non-human mammal or animal cell. Similarly, one preferred test animal for RAMP functional studies is a genetically-modified RAMP1, RAMP2, or RAMP3 humanized mammal. When using any of the above-described samples, appropriately-matched RAMP1–/– or RAMP3–/– non-human mammals or RAMP1–/–, RAMP2–/–, or RAMP3–/– animal cells can be used as negative controls to verify that the agents mediate their effects through the respective RAMP1, RAMP2, or RAMP3 polypeptide.

Direct assessment of RAMP1 polypeptide function can be carried out, for example, by measuring the binding of $^{125}$I-CGRP to cell membranes in vitro (see *Receptor-Ligand Interactions: A Practical Approach*, Ed. E. C. Hulme, IRL Press, Oxford, 1992, McLatchie et al., Nature 393: 333–339, 1998). Plasmid constructs encoding RAMP1 and the CRLR are introduced into host cells by stable or transient transfection using lipofectamine (Gibco BRL, Rockville, Md.) or Fugene™ (Invitrogen, San Diego, Calif.) reagents and following the manufacturer's instructions. Exemplary host cells used for infection include HEK 293 cells, CHO cells, or Swiss3T3 cells. HEK 293 cells are cultured, for example, at 37° C., 5% $CO_2$ in Dulbecco's modified eagle medium supplemented with 10% fetal bovine serum (Gibco BRL). As an example of methods for transient transfection, cells are harvested by nonenzymatic removal from tissue culture plates (Versene, Sigma Chemical Co., St Louis, Mo.) and $5 \times 10^{7-5 \times 10^8}$ cells are incubated with 6 μl Fugene reagent, 10 ug of CRLR DNA and 8 ug of RAMP1 DNA for 20 min. The cells are replated onto T75 flasks and cultured for another 48–72 hrs.

Membranes are prepared, for example, by collecting the transfected host cells into phosphate buffered saline (PBS), pelleting the cells by low speed centrifugation and homogenizing the pellet in homogenization buffer containing 50 mm Hepes-HCl, pH 7.6, 1 mM EDTA, and a protease inhibitor cocktail (e.g., Roche Biosciences, Palo Alto, Calif.). Following centrifugation of the homogenized pellet at low speed (50,000×g at 4° C. for 15 min.) the supernatant is subsequently centrifuged at high speed (50,000×g at 4° C. for 20 min.) and the final pellet is resuspended in the homogenization buffer. Binding assays are carried out in 96 well microtiter plates; 50 ug of membrane protein is incubated with 50 pM $^{125}$I-CGRP1(Amersham, Piscataway, N.J.) in a 100 ul reaction volume. Labeled protein is collected by filtration onto GF/B filters using a cell harvester. The filters are washed in 0.1% polyethylenimine and the amount of label is quantitated in a scintillation counter. Binding affinities are determined by addition of increasing amounts of competing unlabeled CGRP. Assays to assess RAMP2 polypeptide function can be conducted by adapting the above-described assay such that the cells are transfected to express RAMP2 instead of RAMP1. Assays to assess RAMP3 polypeptide function can be conducted by adapting the above described binding assay such that cells are transfected to express RAMP3 instead of RAMP1 and to express the adrenomedulin receptor instead of the CRLR. Similarly, radiolabelled and unlabelled adrenomedulin substitute for radiolabelled and unlabelled CGRP, respectively in the assay to assess RAMP3 function.

RAMP1 or RAMP3 function is also measured at the cellular level, for example, by quantitating the respective CGRP-mediated or adrenomedulin-mediated intracellular cAMP elevations in cells expressing either RAMP1 and the CRLR, or RAMP3 and the adrenomedulin receptor (see *Receptor-Effector Coupling: A Practical Approach*, E. C. Hulme, Ed., IRL Press, Oxford, 1990). RAMP2 function is measured at the cellular level, for example, by measuring intracellular cAMP elevations in cells expressing RAMP2 and CRLR. Adenyl cyclase activation can be measured, for example, using detection assay kits available from commercial vendors (e.g., FlashPlate™ Assay, NEN® Life Science Products, Boston, Mass.). Competition between ($^{125}$I)-labelled cAMP bound to anti-cAMP antibody on the plate and unlabeled cAMP produced by the stimulated cells allows quantitation of the cAMP produced. Transfected cells are prepared, for example, as described above for the binding assay. The cells are seeded in 96 well microtiter Flash-Plates™ at 50,000–100,000 cells per well and preincubated in 100 mm Hepes-HCl, pH 7.6,1 mM CaCl2, 5 mM KCl, 10 mM glucose, and the phosphodiesterase inhibitor IBMX( Sigma). Test agents are added with the CGRP ligand or the adrenomedullin ligand to the cells for 10 min at 37° C., 5% $CO_2$. The reaction is stopped by addition of a permeabilizer detergent (e.g., NP-40) and 0.09% sodium azide. The plate is covered and incubated for minimum of 2 hrs at room temperature and then counted in a microplate scintillation counter.

Another cellular basis for measuring RAMP1 activity is by measuring inward-based current in cells following exposure to CGRP or adrenomedullin, respectively (McLatchie et al., Nature 393: 333–39, 1998). RAMP2 and RAMP3 activity can be measured in a similar manner following exposure to adrenomedullin. For example, the inward current can be measured in Xenopus oocytes, previously transfected with constructs encoding cystic fibrosis transmembrane regulator (CFTR), and either the CRLR and RAMP1, or the adrenomedullin receptor and RAMP2 or RAMP3. Inward current is then assessed following exposure to CGRP, in the case of RAMP1, or following exposure to adrenomedullin, in the case of either RAMP2 or RAMP3.

RAMP1 function can also be assessed in vivo by co-administration of a hepatotoxic agent such as carbon tetrachloride (CTC) to induce liver damage to determine if the RAMP1 modulator counteracts this damage by stimulating RAMP1 activity. The degree of protection afforded by the RAMP1 modulator is assessed by measuring serum AST and ALT activities. This method requires optimization of the following experimental parameters: the amount of CTC administered must be titrated between 35–145 mg/kg to obtain a dose-response curve for elevated AST/ALT levels (Skrzypinska-Gawrysiak et al., Int. J. of Occ. Med. & Environ. Health, 13:165–73, 2000) and the test agent that is a putative RAMP1 modulator is administered at various times prior to and simultaneously with the CTC.

As an alternative to directly assessing the RAMP polypeptide function, agents can be screened for their effect on RAMP1, RAMP2, or RAMP3 expression. This screening method uses cells capable of expressing a RAMP gene (e.g., a cell type that normally expresses an endogenous RAMP1, RAMP2, or RAMP3 gene). The coding sequence linked to the RAMP gene regulatory element(s) in the cell can be either the RAMP gene coding sequence itself or another coding sequence such as a reporter gene sequence. The effects of agents on RAMP1, RAMP2, or RAMP3 expression are assessed by comparing expression of the coding sequence in test animals or cells in the presence and in the absence of the test agent. In one preferred embodiment, the effects of test agents are assessed by measuring LacZ expression in genetically-modified RAMP1+/−, RAMP1−/−, RAMP2+/−, RAMP3+/−, or RAMP3−/− non-human mammals or animal cells which express LacZ, or another reporter gene, as a substitute for the endogenous RAMP1, RAMP2, or RAMP3 coding sequence.

Examples of agents that are screened include, but are not limited to, nucleic acids (e.g., DNA and RNA), carbohydrates, lipids, proteins, peptides, peptidomimetics, small molecules and other agents. Agents can be selected individually for testing or as part of a library. These libraries are obtained using any of the numerous approaches in combinatorial library methods known in the art, and include: biological libraries; spatially addressable parallel solid phase or solution phase libraries; synthetic library methods requiring deconvolution; the "one-bead one-compound " library method; and synthetic library methods using affinity chromatography selection. The biological library approach is limited to peptide libraries, while the other four approaches are applicable to peptide, non-peptide oligomer or small molecule libraries of compounds (e.g., Lam, 1997, Anticancer Drug Des. 12:145; U.S. Pat. Nos. 5,738,996; and 5,807,683).

Examples of methods for the synthesis of molecular libraries can be found in the art, for example, in DeWitt et al., 1993, Proc. Natl. Acad. Sci. USA 90: 6909, Erb et al., 1994, Proc. Natl. Acad. Sci. USA 91: 11422, Zuckermann et al., 1994, J. Med. Chem. 37: 2678, Cho et al., 1993, Science 261: 1303, Carrell et al., 1994, Angew. Chem. Int. Ed. Engl. 33: 2059, Carell et al., 1994, Angew. Chem. Int. Ed. Engl. 33:2061, and Gallop et al., 1994, J. Med. Chem. 37: 1233.

Individual agents or libraries of agents may be presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222:301–310).

Therapeutic Applications

Agents that modulate RAMP1, RAMP2, or RAMP3 can be administered to modulate RAMP1, RAMP2, or RAMP3 activity in the cells that express these genes. Given the role of RAMP1 in liver function and muscle metabolism, agents identified as modulating RAMP1 activity (e.g., agents that stimulate RAMP1 activity) can be used as therapeutics for treating or preventing diseases or conditions, or their symptoms, such as diseases of cardiac, skeletal or smooth muscle, including congestive heart failure, mitral stenosis, acute myocardial infarction, and vascular and cardiovascular disorders such as hypertension. Modulators that increase RAMP1 activity can also be used as therapeutics for treating or preventing hepatocellular disorders, or their symptoms, including chronic and acute hepatitis, hepatomegaly, hepatic steatosis, biliary atresia, gallstones, and chemical or drug-induced hepatotoxicity.

Agents that modulate RAMP1, RAMP2, or RAMP3 activity may be administered by any appropriate route. For example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

When administering therapeutic formulations, the formulations may be in the form of liquid solutions or suspensions, in the form of tablets or capsules, or in the form of powders, nasal drops, or aerosols. Methods well known in the art for making formulations are found, for example, in Remington's Pharmaceutical Sciences (ed. Gennaro, Mack Publishing Co., Easton, Pa., $19^{th}$ ed., 1995).

What is claimed is:

1. A genetically-modified mouse, wherein the genome of said mouse is homozygous for disruption of the RAMP1 gene and wherein said mouse exhibits elevated aminotransferase, alanine aminotransferase, or creatine kinase activity.

2. The mouse of claim 1, wherein said mouse expresses an exogenous reporter gene under the control of the regulatory sequences of said RAMP1 gene.

3. A mouse cell isolated from the mouse of claim 1.

4. The mouse cell of claim 3, wherein said cell is an embryonic stem cell.

* * * * *